(12) United States Patent
McClurken et al.

(10) Patent No.: US 6,702,810 B2
(45) Date of Patent: Mar. 9, 2004

(54) FLUID DELIVERY SYSTEM AND CONTROLLER FOR ELECTROSURGICAL DEVICES

(75) Inventors: Michael E. McClurken, Durham, NH (US); Robert Luzzi, Exeter, NH (US)

(73) Assignee: Tissuelink Medical Inc., Dover, NH (US)

( * ) Notice: Subject to any disclaimer, the term of this patent is extended or adjusted under 35 U.S.C. 154(b) by 0 days.

(21) Appl. No.: 09/797,049

(22) Filed: Mar. 1, 2001

(65) Prior Publication Data

US 2001/0032002 A1 Oct. 18, 2001

Related U.S. Application Data

(60) Provisional application No. 60/187,114, filed on Mar. 6, 2000.

(51) Int. Cl.[7] .................................. A61B 18/18
(52) U.S. Cl. ..................... 606/34; 606/41; 607/105
(58) Field of Search .................. 606/27–34, 37–42, 606/45–52; 607/101–105

(56) References Cited

U.S. PATENT DOCUMENTS

| | | |
|---|---|---|
| 623,022 A | 4/1899 | Johnson |
| 2,002,594 A | 5/1935 | Wappler et al. |
| 3,163,166 A | 12/1964 | Brent et al. |
| 3,901,241 A | 8/1975 | Allen, Jr. |
| 4,037,590 A | 7/1977 | Dohring et al. |
| 4,307,720 A | 12/1981 | Weber, Jr. |
| 4,326,529 A | 4/1982 | Doss et al. |
| 4,567,890 A | 2/1986 | Ohta et al. |
| 4,602,628 A | 7/1986 | Allen, Jr. |
| 4,674,499 A | 6/1987 | Pao |
| 4,920,982 A | 5/1990 | Goldstein |
| 4,985,030 A | 1/1991 | Melzer et al. |
| 5,009,656 A | 4/1991 | Reimels |
| 5,035,696 A | 7/1991 | Rydell |
| 5,071,419 A | 12/1991 | Rydell et al. |
| 5,122,138 A | 6/1992 | Manwaring |
| 5,151,102 A | 9/1992 | Kamiyama et al. |
| 5,156,613 A | 10/1992 | Sawyer |
| 5,167,659 A | 12/1992 | Ohtomo et al. |

(List continued on next page.)

FOREIGN PATENT DOCUMENTS

| | | |
|---|---|---|
| EP | 0 895 756 A1 | 2/1999 |
| EP | 1 095 627 A1 | 5/2001 |
| EP | 1 157 6660 A1 | 11/2001 |

(List continued on next page.)

OTHER PUBLICATIONS

Beer, Edwin, "Removal of Neoplasms of the Urinary Bladder", JAMA., Sep. 9, 1983; 250(10): pp. 1324–1325.

Carter, James, "Suture? Staple? Electrosurgery? How to Decide What is Best For You", JSLS., Apr.–Jun., 1997; 1(2): pp. 171–174.

Matek et al., "Modified Electrocoagulation and Its Possibilities in the Control of Gastrointestinal Bleeding", Endoscopy., Nov., 1979; 11(4): pp. 253–258.

(List continued on next page.)

*Primary Examiner*—Rosiland K. Rollins
(74) *Attorney, Agent, or Firm*—Merchant & Gould P.C.; Mara E. Liepa, Esq.; Michael J. Gallagher, Esq.

(57) ABSTRACT

The invention provides a system for treating tissue that includes a power measurement device, a flow rate controller coupled to the power measurement device, and an electrosurgical device configured and arranged to provide radio frequency power and conductive fluid to the tissue, wherein the flow rate controller is configured and arranged to modify a flow rate of the conductive fluid to the tissue, based on signals from the power measurement device. The invention also provides methods and devices for modifying flow rate of conductive fluid to tissue based on measurement of radio frequency power delivered to the tissue.

30 Claims, 11 Drawing Sheets

U.S. PATENT DOCUMENTS

| | | |
|---|---|---|
| 5,190,541 A | 3/1993 | Abele et al. |
| 5,217,460 A | 6/1993 | Knoepfler |
| 5,242,442 A | 9/1993 | Hirschfeld |
| 5,269,781 A | 12/1993 | Hewell, III |
| 5,277,696 A | 1/1994 | Hagen |
| 5,282,799 A | 2/1994 | Rydell |
| 5,300,087 A | 4/1994 | Knoepfler |
| 5,318,589 A | 6/1994 | Lichtman |
| 5,322,503 A | 6/1994 | Desai |
| 5,334,193 A | 8/1994 | Nardella |
| 5,342,357 A | 8/1994 | Nardella |
| 5,364,394 A | 11/1994 | Mehl |
| 5,395,312 A | 3/1995 | Desai |
| 5,395,363 A | 3/1995 | Billings et al. |
| 5,401,272 A | 3/1995 | Perkins |
| 5,403,311 A | 4/1995 | Abele et al. |
| 5,403,312 A | 4/1995 | Yates et al. |
| 5,405,376 A | 4/1995 | Mulier et al. |
| 5,431,649 A | 7/1995 | Mulier et al. |
| 5,433,708 A | 7/1995 | Nichols et al. |
| 5,437,664 A | 8/1995 | Cohen et al. |
| 5,456,682 A | 10/1995 | Edwards et al. |
| 5,458,596 A | 10/1995 | Lax et al. |
| 5,458,597 A | 10/1995 | Edwards et al. |
| 5,458,598 A | 10/1995 | Feinberg et al. |
| 5,462,521 A | 10/1995 | Brucker et al. |
| 5,472,441 A | 12/1995 | Edwards et al. |
| 5,514,130 A | 5/1996 | Baker |
| 5,536,267 A | 7/1996 | Edwards et al. |
| 5,542,928 A | 8/1996 | Evans et al. |
| 5,558,671 A | 9/1996 | Yates |
| 5,562,703 A | 10/1996 | Desai |
| 5,569,242 A | 10/1996 | Lax et al. |
| 5,584,872 A | 12/1996 | LaFontaine et al. |
| 5,605,539 A | 2/1997 | Buelna et al. |
| 5,609,151 A | 3/1997 | Mulier et al. |
| 5,637,110 A | 6/1997 | Pennybacker et al. |
| 5,643,197 A | 7/1997 | Brucker et al. |
| 5,647,871 A | 7/1997 | Levine et al. |
| 5,653,692 A | 8/1997 | Masterson et al. |
| 5,660,836 A | 8/1997 | Knowlton |
| 5,676,693 A | 10/1997 | LaFontaine |
| 5,681,282 A | 10/1997 | Eggers et al. |
| 5,683,366 A | 11/1997 | Eggers et al. |
| 5,683,384 A | 11/1997 | Gough et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,713,896 A | 2/1998 | Nardella |
| 5,718,701 A | 2/1998 | Shai et al. |
| 5,725,524 A | 3/1998 | Mulier et al. |
| 5,735,846 A | 4/1998 | Panescu et al. |
| 5,746,739 A | 5/1998 | Sutter |
| 5,749,869 A | 5/1998 | Lindenmeier et al. |
| 5,755,753 A | 5/1998 | Knowlton |
| 5,766,153 A | 6/1998 | Eggers et al. |
| 5,800,482 A | 9/1998 | Pomeranz et al. |
| 5,807,395 A | 9/1998 | Mulier et al. |
| 5,810,764 A | 9/1998 | Eggers et al. |
| 5,827,271 A | 10/1998 | Buysse et al. |
| 5,833,703 A | 11/1998 | Manushakian |
| 5,843,019 A | 12/1998 | Eggers et al. |
| 5,843,078 A | 12/1998 | Sharkey |
| 5,843,152 A | 12/1998 | Tu et al. |
| 5,860,951 A | 1/1999 | Eggers et al. |
| 5,860,974 A | 1/1999 | Abele |
| 5,861,002 A | 1/1999 | Desai |
| 5,868,739 A | 2/1999 | Lindenmeier et al. |
| 5,871,469 A | 2/1999 | Eggers et al. |
| 5,873,855 A | 2/1999 | Eggers et al. |
| 5,876,398 A | 3/1999 | Mulier et al. |
| 5,888,198 A | 3/1999 | Eggers et al. |
| 5,891,095 A | 4/1999 | Eggers et al. |
| 5,895,417 A | 4/1999 | Pomeranz et al. |
| 5,897,553 A | 4/1999 | Mulier et al. |
| 5,902,272 A | 5/1999 | Eggers et al. |
| 5,902,328 A | 5/1999 | LaFontaine et al. |
| 5,906,613 A | 5/1999 | Mulier et al. |
| 5,913,854 A | 6/1999 | Maguire et al. |
| 5,913,856 A | 6/1999 | Chia et al. |
| 5,954,716 A | 9/1999 | Sharkey et al. |
| 5,964,755 A | 10/1999 | Edwards |
| 5,976,128 A | 11/1999 | Schilling et al. |
| 5,980,516 A | 11/1999 | Mulier et al. |
| 5,992,418 A | 11/1999 | de la Rama et al. |
| 6,015,407 A | 1/2000 | Rieb et al. |
| 6,016,809 A | 1/2000 | Mulier et al. |
| 6,017,338 A | 1/2000 | Brucker et al. |
| 6,024,733 A | 2/2000 | Eggers et al. |
| 6,027,501 A | 2/2000 | Goble et al. |
| 6,030,379 A | 2/2000 | Panescu et al. |
| 6,032,077 A | 2/2000 | Pomeranz |
| 6,032,674 A | 3/2000 | Eggers et al. |
| 6,045,532 A | 4/2000 | Eggers et al. |
| 6,047,700 A | 4/2000 | Eggers et al. |
| 6,053,172 A | 4/2000 | Hovda et al. |
| 6,053,912 A | 4/2000 | Panescu et al. |
| 6,056,745 A | 5/2000 | Panescu et al. |
| 6,056,747 A | 5/2000 | Saadat et al. |
| 6,063,079 A | 5/2000 | Hovda et al. |
| 6,063,081 A | 5/2000 | Mulier et al. |
| 6,066,134 A | 5/2000 | Eggers et al. |
| 6,071,280 A | 6/2000 | Edwards et al. |
| 6,080,151 A | 6/2000 | Swartz et al. |
| 6,086,585 A | 7/2000 | Hovda et al. |
| 6,093,186 A | 7/2000 | Goble |
| 6,096,037 A | 8/2000 | Mulier et al. |
| 6,102,046 A | 8/2000 | Weinstein et al. |
| 6,105,581 A | 8/2000 | Eggers et al. |
| 6,109,268 A | 8/2000 | Thapliyal et al. |
| 6,113,597 A | 9/2000 | Eggers et al. |
| 6,117,109 A | 9/2000 | Eggers et al. |
| 6,135,999 A | 10/2000 | Fanton et al. |
| 6,142,992 A | 11/2000 | Cheng et al. |
| 6,149,620 A | 11/2000 | Baker et al. |
| 6,159,194 A | 12/2000 | Eggers et al. |
| 6,159,208 A | 12/2000 | Hovda et al. |
| 6,168,594 B1 | 1/2001 | LaFontaine et al. |
| 6,171,275 B1 | 1/2001 | Webster, Jr. |
| 6,174,308 B1 | 1/2001 | Goble et al. |
| 6,174,309 B1 | 1/2001 | Wrublewski et al. |
| 6,176,857 B1 | 1/2001 | Ashley |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,203,542 B1 | 3/2001 | Ellsberry et al. |
| 6,210,402 B1 | 4/2001 | Olsen et al. |
| 6,210,411 B1 | 4/2001 | Hofmann et al. |
| 6,216,704 B1 | 4/2001 | Ingle et al. |
| 6,217,576 B1 | 4/2001 | Tu et al. |
| 6,221,039 B1 | 4/2001 | Durgin et al. |
| 6,224,592 B1 | 5/2001 | Eggers et al. |
| 6,226,554 B1 | 5/2001 | Tu et al. |
| 6,228,078 B1 | 5/2001 | Eggers et al. |
| 6,228,082 B1 | 5/2001 | Baker et al. |
| 6,231,591 B1 | 5/2001 | Desai |
| 6,235,020 B1 | 5/2001 | Cheng et al. |
| 6,236,891 B1 | 5/2001 | Ingle et al. |

| | | |
|---|---|---|
| 6,238,391 B1 | 5/2001 | Olsen et al. |
| 6,238,393 B1 | 5/2001 | Mulier et al. |
| 6,241,753 B1 | 6/2001 | Knowlton |
| 6,254,600 B1 | 7/2001 | Willink et al. |
| 6,258,086 B1 | 7/2001 | Ashley et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,277,112 B1 | 8/2001 | Underwood et al. |
| 6,280,440 B1 | 8/2001 | Gocho |
| 6,283,961 B1 | 9/2001 | Underwood et al. |
| 6,290,715 B1 | 9/2001 | Sharkey et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,302,903 B1 | 10/2001 | Mulier et al. |
| 6,306,134 B1 | 10/2001 | Goble et al. |
| 6,309,387 B1 | 10/2001 | Eggers et al. |
| 6,312,408 B1 | 11/2001 | Eggers et al. |
| 6,315,777 B1 | 11/2001 | Comben |
| 6,322,549 B1 | 11/2001 | Eggers et al. |
| 6,327,505 B1 | 12/2001 | Medhkour et al. |
| 6,328,735 B1 | 12/2001 | Curley et al. |
| 6,328,736 B1 | 12/2001 | Mulier et al. |
| 6,336,926 B1 | 1/2002 | Goble |
| 6,350,276 B1 | 2/2002 | Knowlton |
| 6,355,032 B1 | 3/2002 | Hovda et al. |
| 6,358,248 B1 | 3/2002 | Mulier et al. |
| 6,363,937 B1 | 4/2002 | Hovda et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,402,742 B1 | 6/2002 | Blewett et al. |
| 6,409,722 B1 * | 6/2002 | Hoey et al. .................. 606/34 |
| 6,409,723 B1 | 6/2002 | Edwards |
| 6,416,507 B1 | 7/2002 | Eggers et al. |
| 6,416,508 B1 | 7/2002 | Eggers et al. |
| 6,425,877 B1 | 7/2002 | Edwards |
| 6,432,103 B1 | 8/2002 | Ellsberry et al. |
| 6,461,350 B1 | 10/2002 | Underwood et al. |
| 6,461,354 B1 | 10/2002 | Olsen et al. |
| 6,461,357 B1 | 10/2002 | Sharkey et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,493,589 B1 | 12/2002 | Medhkour et al. |
| 2001/0020167 A1 | 9/2001 | Woloszko et al. |
| 2002/0002393 A1 | 1/2002 | Mitchell |
| 2002/0022870 A1 | 2/2002 | Truckai et al. |
| 2002/0026186 A1 | 2/2002 | Woloszko et al. |
| 2002/0029036 A1 | 3/2002 | Goble et al. |
| 2002/0035361 A1 | 3/2002 | Houser et al. |
| 2002/0049438 A1 | 4/2002 | Sharkey et al. |
| 2002/0049439 A1 | 4/2002 | Mulier et al. |
| 2002/0058933 A1 | 5/2002 | Christopherson et al. |
| 2002/0058935 A1 | 5/2002 | Hoey et al. |
| 2002/0095150 A1 | 7/2002 | Goble |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0115991 A1 | 8/2002 | Edwards |
| 2002/0115992 A1 | 8/2002 | Utley et al. |
| 2003/0004510 A1 | 1/2003 | Wham et al. |

FOREIGN PATENT DOCUMENTS

| | | |
|---|---|---|
| JP | 57-117843 | 7/1982 |
| WO | WO 90/03152 | 4/1990 |
| WO | WO 94/02077 A2 | 2/1994 |
| WO | WO 94/26228 | 11/1994 |
| WO | WO 95/05781 | 3/1995 |
| WO | WO 95/09570 | 4/1995 |
| WO | WO 95/17222 | 6/1995 |
| WO | WO 96/34571 | 11/1996 |
| WO | WO 97/05829 | 2/1997 |
| WO | WO 97/16127 | 5/1997 |
| WO | WO 98/14131 | 4/1998 |
| WO | WO 99/03414 | 1/1999 |
| WO | WO 99/20213 A1 | 4/1999 |
| WO | WO 99/58070 A2 | 11/1999 |
| WO | WO 01/26570 A1 | 4/2001 |
| WO | WO 01/28444 A1 | 4/2001 |
| WO | WO 01/35845 A1 | 5/2001 |
| WO | WO 01/60273 A1 | 8/2001 |

OTHER PUBLICATIONS

Mittleman et al., "Use of the Saline Infusion Electrode Catheter for Improved Energy Delivery and Increased Lesion Size in Radiofrequency Catheter Ablation", PACE., May 1995;18(5 Pt 1): pp. 1022–1027.

Sakatani et al., "Isotonic Mannitol and the Prevention of Local Heat Generation and Tissue Adherence to Bipolar Diathermy Forceps Tips during Electrical Coagulation", J. Neurosurg., Apr. 1995; 82(4): pp. 669–671.

Takao, T., "Effect of Cautery with Irrigation Forceps on the Remnant Liver after Hepatectomy in Rats", Eur. Surg. Res., 1999; 31(2): pp. 173–179.

Yasargil, M.G., "Microsurgery Applied to Neurosurgery", New York: Academic Press, 1969, pp. 41–45.

Yamamoto et al., "New Simple Technique for Hepatic Parenchymal Resection Using a Cavitron Ultrasonic Surgical Aspirator and Bipolar Cautery Equipped with a Channel for Water Dripping", World. J. Surg., Oct. 1999; 23(10): pp. 1032–1037.

Application No. 09/347,635, "Apparatus and Method for Creating, Maintaining, and Controlling a Virtual Electrode Used for the Ablation of Tissue", Hoey et al., filed Jul. 6, 1999.

* cited by examiner

FLUID DELIVERY SYSTEM AND CONTROLLER FOR ELECTROSURGICAL DEVICES

CROSS REFERENCE TO RELATED APPLICATIONS

This application claims the benefit of priority of U.S. Application Serial No. 60/187,114, filed Mar. 6, 2000, the entire disclosure of which is incorporated herein by reference.

FIELD OF THE INVENTION

This invention relates to the field of devices for use in operative surgery upon tissues of the body. More particularly, the invention relates to electrosurgical methods and systems for treatment of body tissues.

BACKGROUND OF THE INVENTION

Electrosurgical devices use electrical energy, most commonly radio frequency (RF) energy, to cut tissue or to cauterize blood vessels. During use, a voltage gradient is created at the tip of the device, thereby inducing current flow and related heat generation in the tissue. With sufficiently high levels of electrical energy, the heat generated is sufficient to cut the tissue and, advantageously, to stop the bleeding from severed blood vessels.

Current electrosurgical devices can cause the temperature of tissue being treated to rise significantly higher than 100° C., resulting in tissue desiccation, tissue sticking to the electrodes, tissue perforation, char formation and smoke generation. Peak tissue temperatures as a result of RF treatment of target tissue can be as high as 320° C., and such high temperatures can be transmitted to adjacent tissue via thermal diffusion. Undesirable results of such transmission to adjacent tissue include unintended thermal damage to the tissue.

Using saline to couple RF electrical energy to tissue prevents such undesirable effects as sticking, desiccation, smoke production and char formation. One key factor is preventing tissue desiccation, which occurs if tissue temperature exceeds 100° C. and all of the intracellular water boils away, leaving the tissue extremely dry and much less electrically conductive. However, an uncontrolled flow rate of saline can provide too much cooling at the electrode/tissue interface. This cooling reduces the temperature of the target tissue being treated, and the rate at which tissue thermal coagulation occurs is determined by tissue temperature. This, in turn, can result in longer treatment time, to achieve the desired tissue temperature for cauterization or cutting of the tissue. Long treatment times are undesirable for surgeons since it is in the best interest of the patient, physician and hospital to perform surgical procedures as quickly as possible.

RF energy delivered to tissue is unpredictable and often not optimal when using general-purpose generators. Most general-purpose RF generators have modes for different waveforms (cut, coagulation, or a blend of these two) and device types (monopolar, bipolar), as well as power levels that can be set in watts. However, once these settings are chosen, the actual power delivered to tissue can vary dramatically over time as tissue impedance changes over the course of RF treatment. This is because the power delivered by most generators is a function of tissue impedance, with the power ramping down as impedance either decreases toward zero or increases significantly to several thousand ohms.

A further limitation of current electrosurgical devices arises from size constraints of the device in comparison to tissue that is encountered during a single surgical procedure. During the course of a single procedure, for example, a surgeon often encounters a wide variety of tissue sizes. Surgical devices often come in a variety of sizes because larger segments of tissue physically require commensurately larger electrode jaws or tips, but smaller segments of tissue often are not optimally treated by the much larger size RF device. It is undesirable to require numerous surgical devices during a single procedure, because this wastes valuable operating room time, can make it difficult to precisely relocate the treatment site, increases the risk of infection, and increases the cost by increasing the number of different surgical devices that are needed to complete the surgical procedure.

For example, a bipolar saline-enhanced tissue sealing forceps that has jaws long enough to effectively seal a 30 mm length of tissue may not be desirable for sealing a segment of tissue that is 10 mm in length. Excess saline from one of the electrode jaws (for a bipolar device) can flow to the other electrode in the space where there is no intervening tissue. This flow of electrically conductive saline can act as an electrical resistor in parallel with the electrical pathway through the target tissue. Electrical current flow through the saline can divert or shunt RF energy away from going through the target tissue, and slow down the rate at which the target tissue is heated and treated.

A surgeon may first be sealing and cutting lung tissue as part of a wedge resection using the full 30 mm jaw length 2–3 times to remove a tip of a lobe of lung for biopsy. If the intraoperative histopathology indicates that the suspected tissue has a malignant tumor, then the surgeon may convert the procedure to a lobectomy. As part of the lobectomy the surgeon will want to seal and cut large blood vessels that supply the lobe. Alternatively, the surgeon may want to toughen up or coagulate large vessels with RF and then apply a ligating clip to assure hemostasis before cutting. Even compressed, these blood vessels might only fill a small fraction of the 30 mm length of electrode jaw. For at least the reasons identified above, this is an undesirable situation with current electrosurgical devices.

SUMMARY OF THE INVENTION

The invention provides a system for treating tissue comprising a power measurement device, a flow rate controller coupled to the power measurement device, and an electrosurgical device configured and arranged to provide radio frequency power and conductive fluid to the tissue, wherein the flow rate controller is configured and arranged to modify a flow rate of the conductive fluid to the tissue, based on signals from the power measurement device.

Preferably, the flow rate controller modifies the flow rate of the conductive fluid to the tissue based on heat used to warm the conductive fluid and heat used to convert the conductive fluid to vapor. In a preferred embodiment, the flow rate controller modifies the flow rate of the conductive fluid to the tissue using the relationship:

$$K = \frac{1}{\{\rho c_p \Delta T + \rho h_v Q_b / Q_l\}}$$

In another embodiment, the invention provides a device for modifying flow rate of conductive fluid to tissue based on measurement of radio frequency power delivered to the tissue, the device comprising a flow rate controller configured and arranged to modify flow rate of the conductive fluid to the tissue, based on heat used to warm the conductive fluid and heat used to convert the conductive fluid to vapor. Preferably, the device modifies the flow rate of the conductive fluid to the tissue using the relationship:

$$K = \frac{1}{\{\rho c_p \Delta T + \rho h_v Q_b / Q_l\}}$$

In an alternative embodiment, the invention provides a device for treating tissue using radio frequency power and conductive fluid, the device comprising a sensing device, and a processor coupled to the sensing device, wherein the processor is configured and arranged to adjust flow rate of the conductive fluid to the tissue, by determining a level of radio frequency power applied to the tissue using the sensing device, and adjusting the flow rate of the conductive fluid to the tissue. Preferably, the processor is configured and arranged to adjust the flow rate of the conductive fluid to the tissue based on heat used to warm the conductive fluid and heat used to convert the conductive fluid to vapor. Preferably, the flow rate controller modifies the flow rate of the conductive fluid to the tissue using the relationship:

$$K = \frac{1}{\{\rho c_p \Delta T + \rho h_v Q_b / Q_l\}}$$

In another embodiment, the invention provides a method for treating tissue comprising applying radio frequency power and conductive fluid to the tissue using a surgical device, wherein the conductive fluid is provided to the tissue at a fluid flow rate, determining an amount of radio frequency power applied to the tissue, and modifying the fluid flow rate based on the power applied to the tissue. Preferably, the step of modifying the fluid flow rate based on the power applied to the tissue comprises modifying the flow rate of the conductive fluid to the tissue based on heat used to warm the conductive fluid and heat used to convert the conductive fluid to vapor. Preferably, the step of modifying the fluid flow rate based on the power applied to the tissue comprises determining the fluid flow rate using the relationship:

$$K = \frac{1}{\{\rho c_p \Delta T + \rho h_v Q_b / Q_l\}}$$

In an alternative embodiment, the invention provides a method for treating tissue comprising providing a surgical device comprising an electrode, wherein the surgical device is configured and arranged to receive radio frequency power and conductive fluid and deliver the radio frequency power and conductive fluid to the tissue, determining the radio frequency power applied to the tissue, and providing the conductive fluid to the tissue at a fluid flow rate, wherein the fluid flow rate is modified to control boiling of the conductive fluid at the tissue. Preferably, the step of providing the conductive fluid to the tissue at a fluid flow rate comprises providing the conductive fluid to the tissue based on heat used to warm the conductive fluid and heat used to convert the conductive fluid to vapor. In a preferred embodiment, the step of providing the conductive fluid to the tissue at a fluid flow rate comprises providing the conductive fluid to the tissue using the relationship:

$$K = \frac{1}{\{\rho c_p \Delta T + \rho h_v Q_b / Q_l\}}$$

In another embodiment, the invention provides a system for treating tissue comprising a power measurement device, a flow rate controller coupled to the power measurement device, a flow control device coupled to the flow rate controller, and an electrosurgical device coupled to the flow control device and the power measurement device, wherein the electrosurgical device is configured and arranged to provide radio frequency power and conductive fluid to the tissue, and wherein the flow rate controller is configured and arranged to modify a flow rate of the conductive fluid to the electrosurgical device, based on signals from the power measurement device. Preferably, the flow control device comprises a pump. In one embodiment, the pump comprises a peristaltic pump. In another embodiment, the pump comprises a syringe pump. Preferably, the electrosurgical device comprises a bipolar electrosurgical device.

According to this embodiment, the flow rate controller is preferably configured and arranged to modify the flow rate of the conductive fluid to the flow control device based on heat used to warm the conductive fluid and heat used to convert the conductive fluid to vapor. In a preferred embodiment, the flow rate controller is configured and arranged to modify the flow rate of the conductive fluid to the tissue using the relationship:

$$K = \frac{1}{\{\rho c_p \Delta T + \rho h_v Q_b / Q_l\}}$$

The invention can improve the speed of tissue coagulation provided by fluid-enhanced electrosurgery by assuring that the electrode-tissue interface is within a desired temperature range (for example, not significantly hotter than 100° C.) through the control of the fraction of conductive fluid that is boiled off at the electrode-tissue interface. This improvement can be achieved by measuring power provided to the device and regulating the flow of fluid to the device. Preferably, tissue sensors (for example, that would measure tissue temperature or tissue impedance) are not required according to the invention.

Some embodiments of the invention can provide one or more advantages, such as the ability to achieve the desired tissue effect (for example, coagulation, cutting, or the like) in a fast, effective manner. The invention can also provide the ability to treat tissue quickly without using a tissue sensor (for example, a temperature sensor) built into the device or a custom special-purpose generator. The invention can allow a surgeon to use a variety of electrosurgical devices with a wide variety of general-purpose generators. Further, the invention can provide the ability to use an electrosurgical device that is capable of quickly and effectively sealing a wide variety of tissue sizes and thicknesses.

DETAILED DESCRIPTION OF THE PREFERRED EMBODIMENTS

Overview

The invention provides a system, device and methods that preferably improve control of tissue temperature at a treatment site during a medical procedure. The invention is particularly useful during surgical procedures upon tissues of the body, where tissue is often cut and coagulated. The invention involves the use of electrosurgical procedures, which utilize RF power and conductive fluid to treat tissue. Preferably, a desired tissue temperature range is achieved through adjusting parameters, such as conductive fluid flow rate, that affect the temperature at the tissue/electrode interface. Preferably, the device achieves a desired tissue temperature utilizing a desired percentage boiling of the conductive solution at the tissue/electrode interface. In a preferred embodiment, the invention provides a control device, the device comprising a flow rate controller that receives a signal indicating power applied to the system, and adjusts the flow rate of conductive fluid from a fluid source to an electrosurgical device. The invention also contemplates a control system comprising a flow rate controller, a measurement device that measures power applied to the system, and a pump that provides fluid at a desired flow rate.

Figure 1:
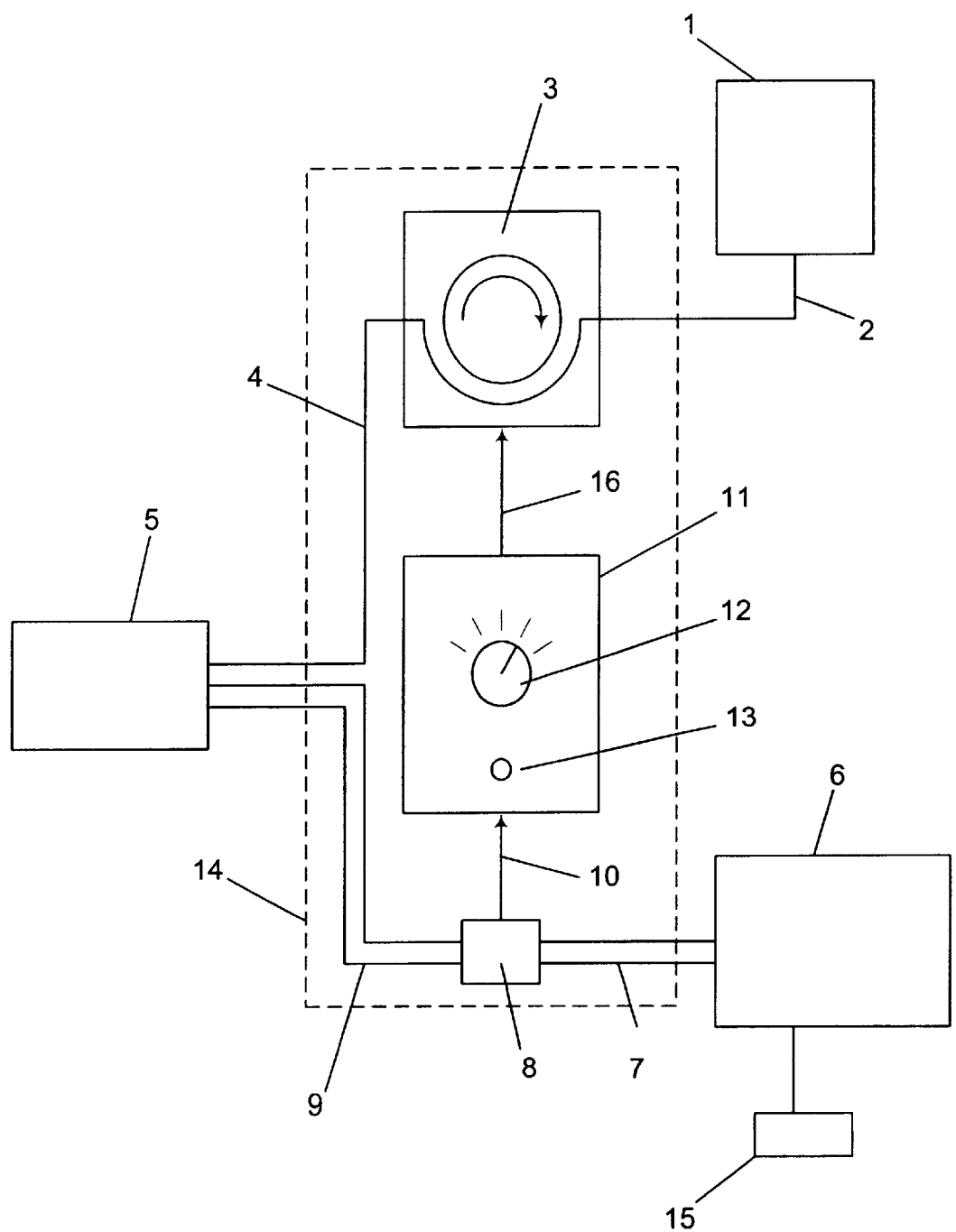
FIG. 1 is a block diagram showing one embodiment of the overall control system of the invention, and an electrosurgical device.

The invention will be discussed generally with reference to FIG. 1. FIG. 1 shows a block diagram of one embodiment of a system of the invention. As shown in FIG. 1, conductive fluid is provided from a fluid source 1, through a fluid line 2, to a pump 3, which has an outlet fluid line 4 that is connected to an electrosurgical device 5. In a preferred embodiment, the conductive fluid comprises saline, such as sterile, normal saline. Although the description herein will describe saline as a conductive fluid, one of skill in the art would understand, upon reading this disclosure, that other conductive fluids can be used in accordance with the invention. The conductive fluid can comprise physiologic saline ("normal" saline, or 0.9% NaCl solution), lactated Ringer's™, or the like.

A generator 6 provides RF energy via a cable 7 to a power measurement device 8 that measures the RF electrical power. In this embodiment, the power measurement device 8 does not turn the power off or on or alter the power in any way. A power switch 15 connected to the generator 6 is provided by the generator manufacturer and is used to turn the generator 6 on and off. The power switch 15 can comprise any switch to turn the power on and off, and is commonly provided in the form of a footswitch or other easily operated switch. A cable 9 carries RF energy from the power measurement device 8 to the electrosurgical device 5. Power is preferably measured before it reaches the electrosurgical device.

A flow rate controller 11 includes a selection switch 12 that can be set to achieve desired levels of percentage fluid boiling (for example, 100%, 98%, 80% boiling). The flow rate controller 11 receives a signal 10 from the power measurement device 8 and calculates the correct fluid flow rate based on percentage boiling indicated by the selection switch 12. In a preferred embodiment, a fluid switch 13 is provided so that the fluid system can be primed (air eliminated) before turning the generator 6 on. The output signal 16 of the flow rate controller 11 is sent to the pump 3 motor to regulate the flow rate of conductive fluid, and thereby provide an appropriate fluid flow rate for the amount of power being delivered.

Throughout the present description, like reference numerals and letters indicate corresponding structure throughout the several views, and such corresponding structure need not be separately discussed.

In one embodiment, the invention comprises a flow rate controller that is configured and arranged to be connected to a source of RF power, and a source of conductive fluid. The device of the invention receives information about the level of RF power applied to an electrosurgical device, and adjusts the flow rate of the conductive fluid to the electrosurgical device, thereby controlling temperature at the tissue treatment site.

In another embodiment, elements of the system are physically included together in one electronic enclosure. One such embodiment is shown by enclosure within the outline box 14 of FIG. 1. In the illustrated embodiment, the pump 3, flow rate controller 11, and power measurement device 8 are enclosed within an enclosure, and these elements are connected through electrical connections to allow signal 10 to pass from the power measurement device 8 to the flow rate controller 11, and signal 16 to pass from the flow rate controller 11 to the pump 3. Other elements of a system can also be included within one enclosure, depending upon such factors as the desired application of the system, and the requirements of the user.

The pump 3 can be any suitable pump used in surgical procedures to provide saline or other fluid at a desired flow rate. Preferably, the pump 3 comprises a peristaltic pump. Alternatively, pump 3 can be a "syringe pump," with a built-in fluid supply; or a double-acting syringe pump with two syringes such that they can draw saline from a reservoir. Conductive fluid can also be provided from an intravenous ("I.V.") bag full of saline that flows under the influence of gravity to the pump 3. Similar pumps can be used in connection with the invention, and the illustrated embodiments are exemplary only. The precise configuration of the pump 3 is not critical to the invention. In some embodiments, the pump can be substituted with any type of flow controller, to allow the user to control the flow rate of conductive fluid to the device. Alternatively, a valve configuration can be substituted for pump 3.

The components of the system will now be described in detail.

The Flow Rate Controller

The flow rate controller 11 controls the rate of flow from the fluid source 1, based upon the amount of RF power provided from the generator 6 to the electrosurgical device 5. The flow rate of conductive fluid, such as saline, interacts with the RF power and various modes of heat transfer away from the target tissue, as described herein.

Figure 2:
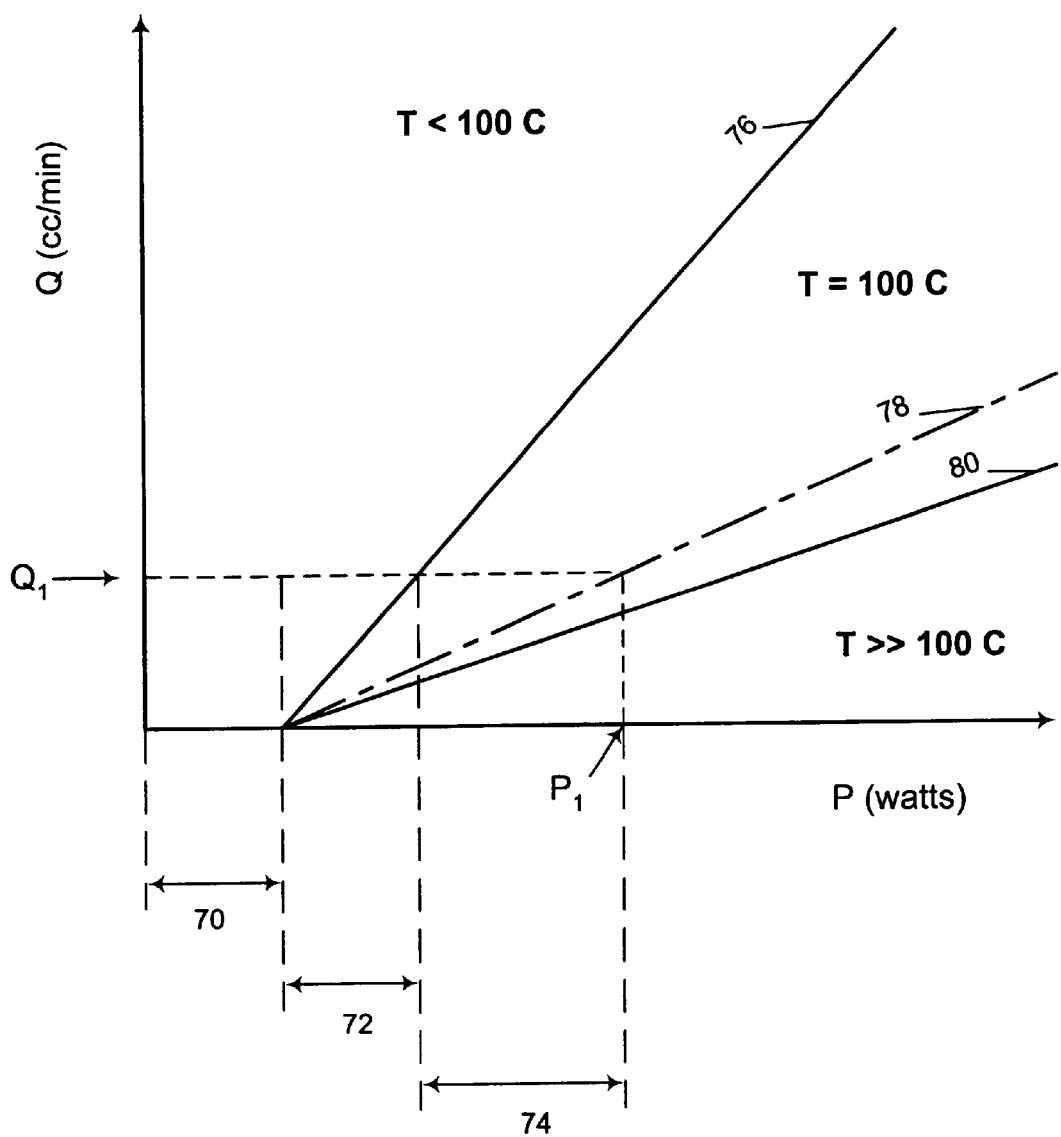
FIG. 2 is a schematic graph that describes the relationship between RF power to tissue (P), flow rate of saline (Q), and tissue temperature (T).

FIG. 2 shows a schematic graph that describes the relationship between the flow rate of saline, RF power to tissue, and regimes of boiling. Based on a simple one-dimensional lumped parameter model of the heat transfer, the peak tissue temperature can be estimated, and once tissue temperature is estimated, it follows directly whether it is hot enough to boil saline.

$$P = \Delta T/R + \rho c_p Q_1 \Delta T + \rho Q_b h_v \quad (1)$$

Where P=the total RF electrical power that is converted into heat.

Conduction.

The first term [$\Delta T/R$] in equation (1) is heat conducted to adjacent tissue, represented as 70 in FIG. 2, where:

$\Delta T = (T - T_\infty)$ the difference in temperature between the peak tissue temperature (T) and the normal temperature ($T_\infty$) of the body tissue (° C.). Normal temperature of the body tissue is generally 37° C.; and R=Thermal Resistance of surrounding tissue, the ratio of the temperature difference to the heat flow (° C./watt).

This thermal resistance can be estimated from published data gathered in experiments on human tissue (Phipps, J. H., "Thermometry studies with bipolar diathermy during hysterectomy," *Gynaecological Endoscopy*, 3:5–7 (1994)). As described by Phipps, Kleppinger bipolar forceps were used with an RF power of 50 watts, and the peak tissue temperature reached 320° C. For example, using the energy balance of equation (1), and assuming all the RF heat put into tissue is conducted away, then R can be estimated:

$$R = \Delta T/P = (320 - 37)/50 = 5.7 \approx 6° \text{ C./watt}$$

However, it is undesirable to allow the tissue temperature to reach 320° C., since tissue will become desiccated. At a temperature of 320° C., the fluid contained in the tissue is typically boiled away, resulting in the undesirable tissue effects described herein. Rather, it is preferred to keep the peak tissue temperature at no more than 100° C. to prevent desiccation of the tissue. Assuming that saline boils at 100° C., the first term in equation (1) ($\Delta T/R$) is equal to (100−37)/6=10.5 watts. Thus, based on this example, the maximum amount of heat conducted to adjacent tissue without any significant risk of tissue desiccation is 10.5 watts.

Referring to FIG. 2, RF power to tissue is represented on the X-axis as P (watts) and flow rate of saline (cc/min) is represented on the Y-axis as Q. When the flow rate of saline equals zero (Q=0), there is an "offset" RF power that shifts the origin of the sloped lines 76, 78, and 80 to the right. This offset is the heat conducted to adjacent tissue. For example, using the calculation above for bipolar forceps, this offset RF power is about 10.5 watts. If the power is increased above this level with no saline flow, the peak tissue temperature can rise well above 100° C., resulting in tissue desiccation from the boiling off of water in the cells of the tissue.

Convection.

The second term [$\rho c_p Q_1 \Delta T$] in equation (1) is heat used to warm up the flow of saline without boiling the saline, represented as 72 in FIG. 2, where:

ρ=Density of the saline fluid that gets hot but does not boil (approximately 1.0 gm/cm³);

$c_p$=Specific heat of the saline (approximately 4.1 watt-sec/gm-° C.);

$Q_1$=Flow rate of the saline that is heated (cm³/sec); and $\Delta T$=Temperature rise of the saline. Assuming that the saline is heated to body temperature before it gets to the electrode, and that the peak saline temperature is similar to the peak tissue temperature, this is the same $\Delta T$ as for the conduction calculation above.

The onset of boiling can be predicted using equation (1) with the last term on the right set to zero (no boiling) ($\rho Q_b h_v = 0$), and solving equation (1) for $Q_1$ leads to:

$$Q_1 = [P - \Delta T/R]/\rho c_p \Delta T \quad (2)$$

This equation defines the line shown in FIG. 2 as the line of onset of boiling 76. It is possible in some embodiments that the flow of conductive fluid can be nonuniformly heated, thereby reducing the term in the denominator of Equation (2), $\rho c_p \Delta T$. If the amount of convection is less due to nonuniformity of heating, conductive fluid boiling would occur sooner. In other words, the slope of the curve will be steeper at a given power, and conductive fluid will boil at a lower flow rate. This type of nonuniformity can be associated with device configurations and hence could be used to provide a level of control of convection. For example, for a particular type of device known to provide nonuniform heating of the conductive solution, the invention can provide an "offset" to take this into account to provide the desired level of boiling at the electrode/tissue interface.

Boiling.

The third term [$\rho Q_b h_v$] in equation (1) relates to heat that goes into converting liquid saline to vapor saline and is represented as 74 in FIG. 2, where:

$Q_b$=Flow rate of saline that boils (cm³/sec); and $h_v$=Heat of vaporization of saline (approximately 2,000 watt-sec/gm).

A flow rate of only 1 cc/min will absorb a significant amount of heat if it is completely boiled, or about $\rho Q_b h_v = (1)(1/60)(2,000) = 33.3$ watts. The heat needed to warm this flow rate from body temperature to 100° C. is much less, or $\rho c_p Q_1 \Delta T = (1)(4.1)(1/60)(100-37) = 4.3$ watts. In other words, the most significant factor contributing to heat transfer from a wet electrode device can be fractional boiling. The present invention recognizes this fact and exploits it.

Fractional boiling can be described by equation (3) below:

$$Q_1 = \frac{\{P - \Delta T/R\}}{\{\rho c_p \Delta T + \rho h_v Q_b / Q_l\}} \quad (3)$$

If the ratio of $Q_b/Q_1$ is 0.50 this is the 50% boiling line 78 shown in FIG. 2. If the ratio is 1.0 this is the 100% boiling line 80 shown in FIG. 2.

Control Strategy

Figure 3:
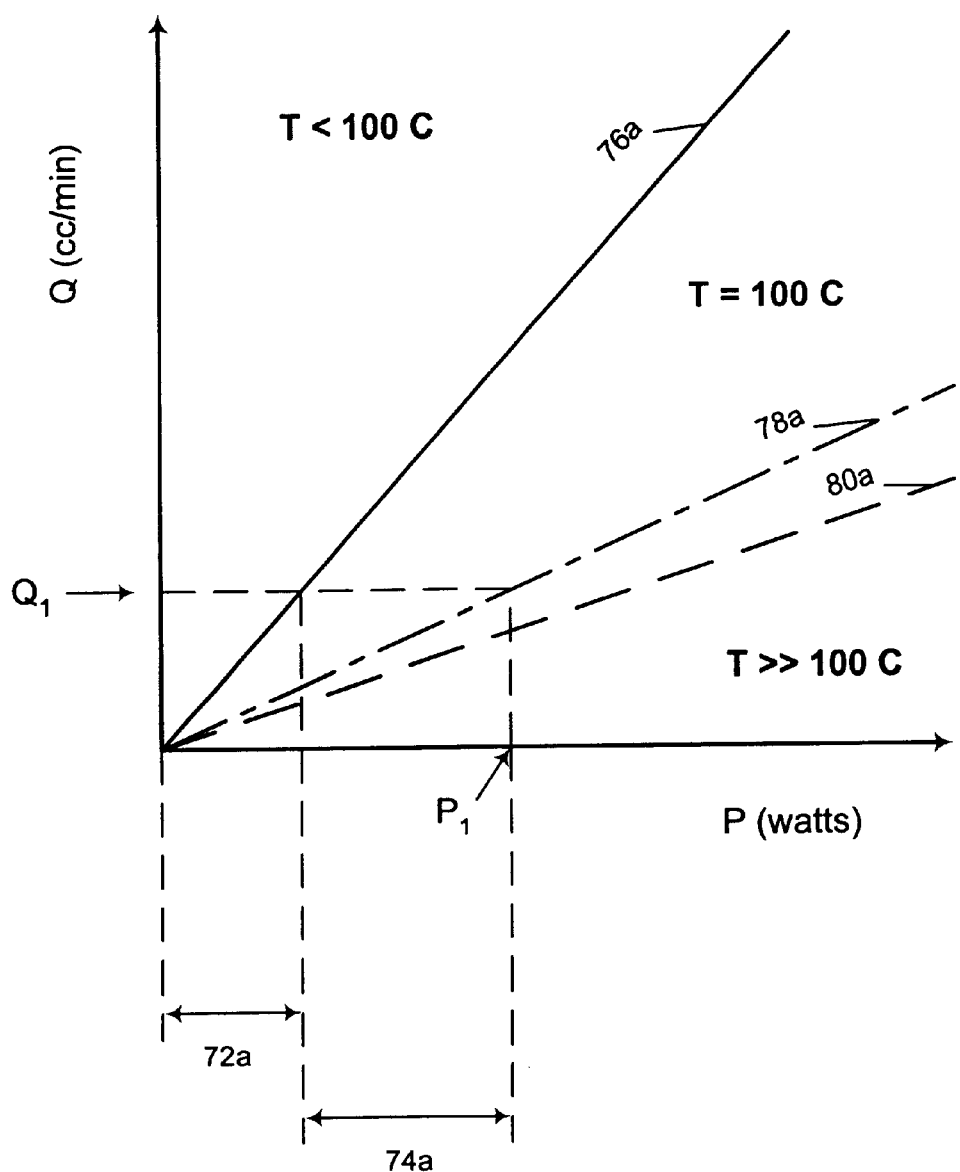
FIG. 3 is schematic graph that describes the relationship between RF power to tissue (P), flow rate of saline (Q), and tissue temperature (T) when heat conduction to adjacent tissue is neglected.

Since the amount of heat conducted away to adjacent tissue is difficult to precisely predict, it is preferable, from a control point of view, to assume the worst case situation of zero heat conduction, and provide enough saline so that if necessary, all the RF power could be used to heat up and boil the saline, thus providing that the peak tissue temperature will not go over 100° C. a significant amount. This situation is shown in the schematic graph of FIG. 3.

It is desirable to control the saline flow rate so that it is always on a "line of constant % boiling" for consistent tissue effect. If the device is monopolar and shunting through saline is not an issue, then it can be preferable to operate close to, but not over the line of the onset of boiling, 76a in FIG. 3. This preferably keeps tissue as hot as possible with causing desiccation. Alternatively, if the device is bipolar and shunting of electrical energy through excess saline is an issue, then it can be preferable to operate along a line of constant boiling such as line 78a in FIG. 3, the 50% line. This simple proportional control will have the flow rate determined by equation (4), where K is the proportionality constant:

$$Q_1 = K \times P \quad (4)$$

In essence, when power P goes up, the flow rate Q will be proportionately increased. Conversely, when power P goes down, the flow rate Q will be proportionately decreased.

K is primarily dependent on the fraction of saline that boils, as shown in equation (5), which is equation (3) solved for K after eliminating P using equation (4), and neglecting the conduction term ($\Delta T/R$):

$$K = \frac{1}{\{\rho c_p \Delta T + \rho h_v Q_b / Q_l\}} \quad (5)$$

Thus, the present invention provides a method of controlling boiling of conductive fluid at the tissue/electrode interface. In a preferred embodiment, this provides a method of treating tissue without use of tissue sensors, such as temperature or impedance sensors. Preferably, the invention can control boiling of conductive fluid at the tissue/electrode interface and thereby control tissue temperature without the use of feedback loops.

Figure 4:
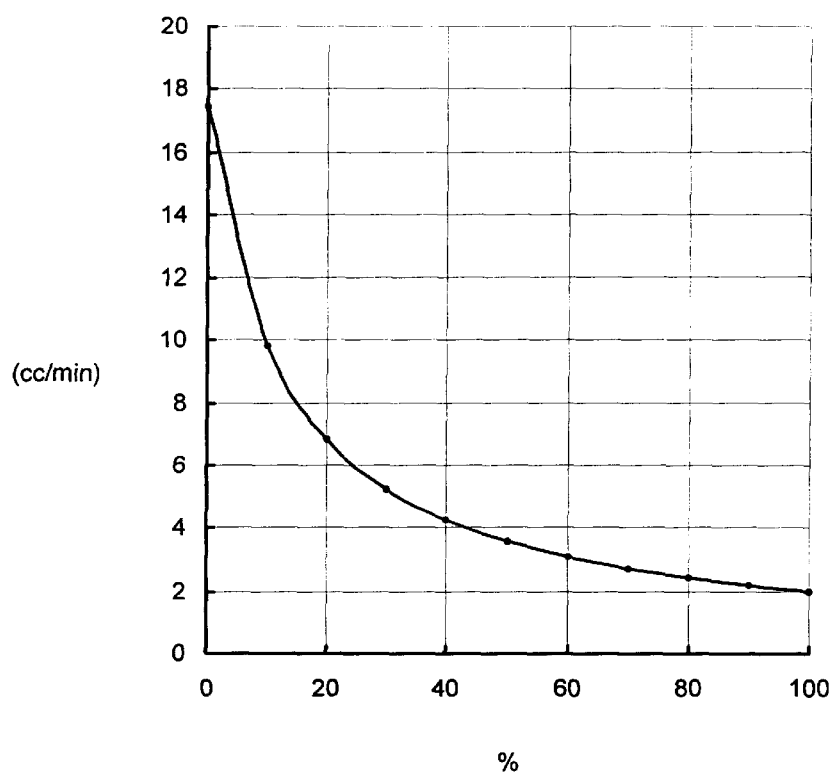
FIG. 4 is a graph showing the relationship of percentage saline boiling and saline flow rate (cc/min) for an exemplary RF generator output of 75 watts.

FIG. 4 shows an exemplary graph of flow rate versus % boiling for a situation where the RF power is 75 watts. The percent boiling is represented on the X-axis, and the saline flow rate (cc/min) is represented on the Y-axis. According to this example, at 100% boiling the most desirable saline flow rate is 2 cc/min.

As discussed herein, RF energy delivery to tissue can be unpredictable and vary with time, even though the generator has been "set" to a fixed wattage.

Figure 5:
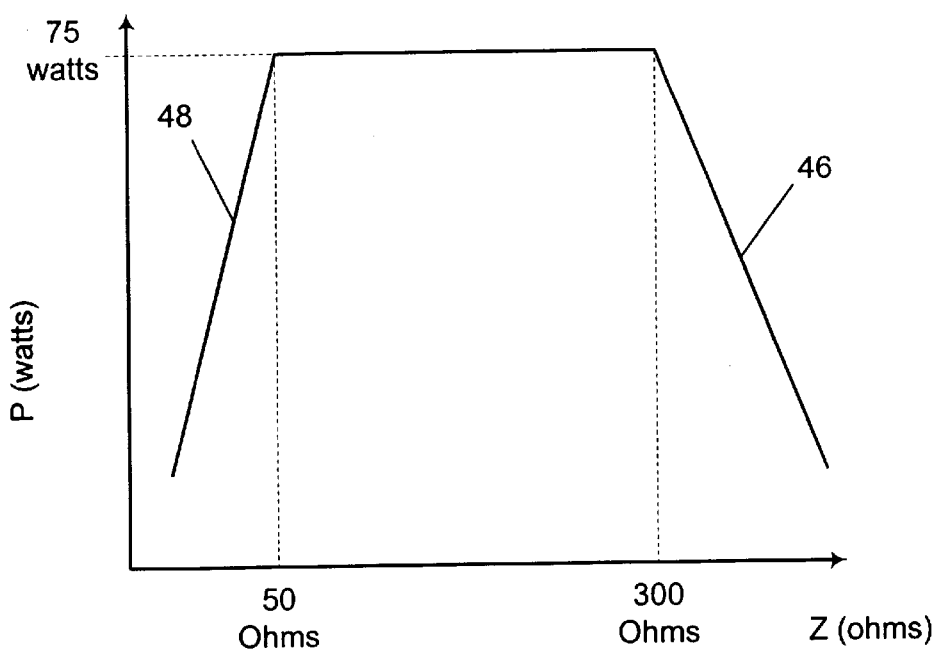
FIG. 5 is a schematic graph that describes the relationship of load impedance (Z, in ohms) and generator output power (P, in watts), for an exemplary generator output of 75 watts in a bipolar mode.

The schematic graph of FIG. 5 shows the general trends of the output curve of a typical general-purpose generator, with the output power changing as load (tissue plus cables) impedance changes. Load impedance (in ohms) is represented on the X-axis, and generator output power (in watts) is represented on the Y-axis. In the illustrated embodiment, the electrosurgical power (RF) is set to 75 watts in a bipolar mode. As shown in the figure, the power will remain constant as it was set as long as the impedance stays between two cut-offs of impedance, that is, between 50 ohms and 300 ohms in the illustrated embodiment. Below load impedance of 50 ohms, the power will decrease, as shown by the low impedance ramp 48. Above load impedance of 300 ohms, the power will decrease, as shown by the high impedance ramp 46. Of particular interest to saline-enhanced electrosurgery is the low impedance cut-off (low impedance ramp 48), where power starts to ramp down as impedance drops further.

Figure 6:
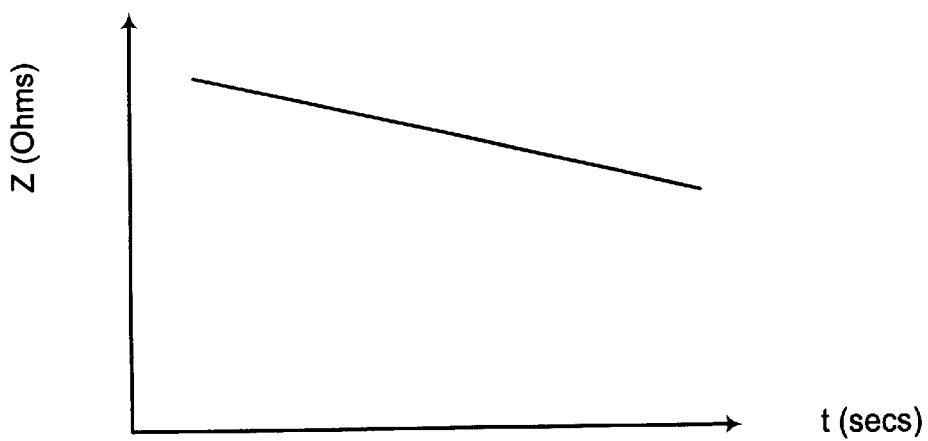
FIG. 6 is a schematic graph that describes the relationship of time (t, in seconds) and tissue impedance (Z, in ohms) after RF activation.

FIG. 6 shows the general trend of how tissue impedance generally changes with time for saline-enhanced electrosurgery. As tissue heats up, the temperature coefficient of the tissue and saline in the cells is such that the tissue impedance decreases. Thus, as tissue heats up, the load impedance decreases, approaching the impedance cut-off of 50 ohms. Once tissue is sufficiently heated, such that the impedance cut-off is passed, the power decreases along the lines of the low impedance ramp 48 of FIG. 5.

Combining the effects shown in FIG. 5 and FIG. 6, it becomes clear that when using a general-purpose generator set to a "fixed" power, the actual power delivered can change dramatically over time as tissue heats up and impedance drops. Looking at FIG. 5, if the impedance drops from 100 to 75 ohms over time, the power output would not change because the curve is "flat" in that region of impedances. If, however, the impedance drops from 75 to 30 ohms one would "turn the corner" onto the low impedance ramp 48 portion of the curve and the power output would decrease dramatically.

According to the invention, the control device receives a signal indicating the drop in actual power delivered to the tissue and adjusts the flow rate of saline to maintain the tissue/electrode interface at a desired temperature. In a preferred embodiment, the drop in actual power delivered is sensed by the power measurement device 8 (shown in FIG. 1), and the flow rate of saline is decreased by the flow rate controller 11 (also shown in FIG. 1). Preferably, this reduction in saline flow rate allows the tissue temperature to stay as hot as possible without desiccation. If the control device was not in operation and the flow rate allowed to remain higher, the tissue would be over-cooled at the lower power input. This would result in decreasing the temperature of the tissue at the treatment site.

The flow rate controller 11 of FIG. 1 can be a simple "hard-wired" analog or digital device that requires no programming by the user or the manufacturer. The flow rate controller 11 can alternatively include a processor, with or without a storage medium, in which the determination procedure is performed by software, hardware, or a combination thereof. In another embodiment, the flow rate controller 11 can include semi-programmable hardware configured, for example, using a hardware descriptive language, such as Verilog. In another embodiment, the flow rate controller 11 of FIG. 1 is a computer, microprocessor-driven controller with software embedded. In yet another embodiment, the flow rate controller 11 can include additional features, such as a mechanism to automatically keep the saline flow on for several seconds after the RF is turned off to provide a post-coagulation cooling of the tissue or "quench," which can increase the strength of the tissue seal.

As discussed herein, the saline can act as a shunt and divert energy away from target tissue. This is a phenomenon that can only occur with a bipolar device. In a monopolar device, saline can "pool" in the treatment area, and can, in some situations, divert energy by pooling. For the present discussion, shunting in connection with a bipolar device will be discussed.

In order to describe the underlying issue of saline shunting, an exemplary bipolar endoscopic electrosurgical device will be described in some detail. The bipolar electrosurgical device is described for purposes of illustrating the invention only, and it is understood that a wide variety of electrosurgical devices can be used in connection with the invention.

Preferably, the control device of the invention is used in connection with an electrosurgical device that is capable of controlling saline flow (for example, by controlling the location from which the saline is released from the electrosurgical device to the tissue). Any electrosurgical device that is capable of controlling saline flow is preferably used in connection with the invention described herein.

Figure 7:
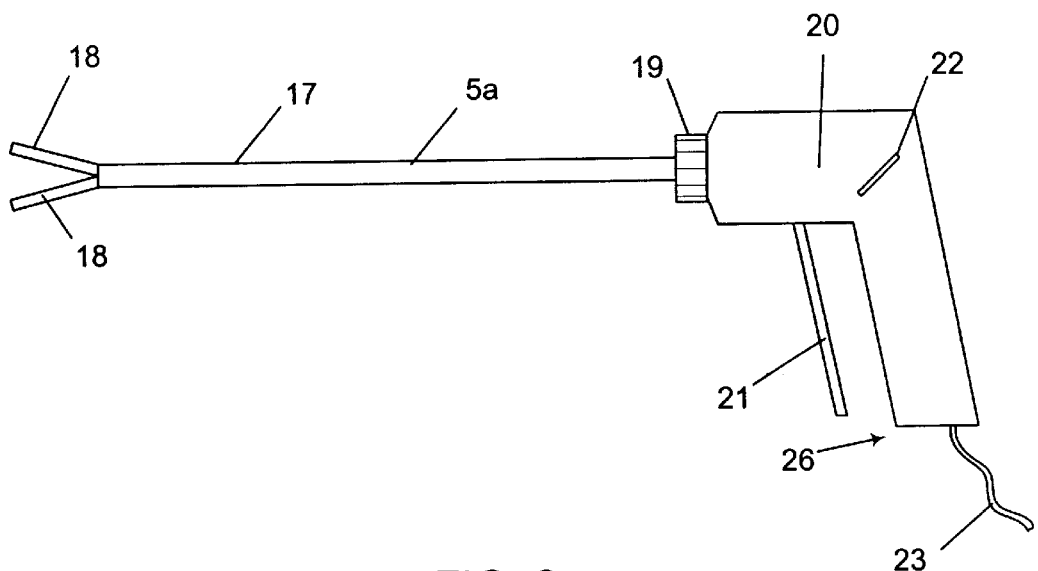
FIG. 7 is a schematic side view of one embodiment of a bipolar electrosurgical device.

FIG. 7 shows an overall simple side schematic view of one embodiment of an electrosurgical device 5a that is designed to grasp, coagulate and then cut tissue. The electrosurgical device 5a includes a shaft 17, two opposing jaws 18 at the distal tip of the shaft 17, a collar 19 for rotating the entire shaft, a proximal handle 20, an actuation lever 21 which when squeezed will close the opposing jaws 18, a pair of paddles 22 to activate the built-in cutting mechanism (not shown in the figure), and a cable 23 attached to the handle that contains two electrical wires and one fluid channel (not shown individually in the figure). In use, tissue to be treated is positioned between the jaws 18 of the device 5a. The actuation lever 21 is then moved in direction of arrow 26, thereby drawing the opposing jaws 18 toward each other, to close the jaws 18 on the tissue. RF energy and conductive fluid, such as saline, are applied through the device and to the treatment site, thereby heating the tissue to coagulate, or achieve the desired treatment of the tissue. If desired, after coagulating the tissue between the jaws, the jaws can be held clamped together and the cutting mechanism can be actuated to cut tissue.

Figure 8:
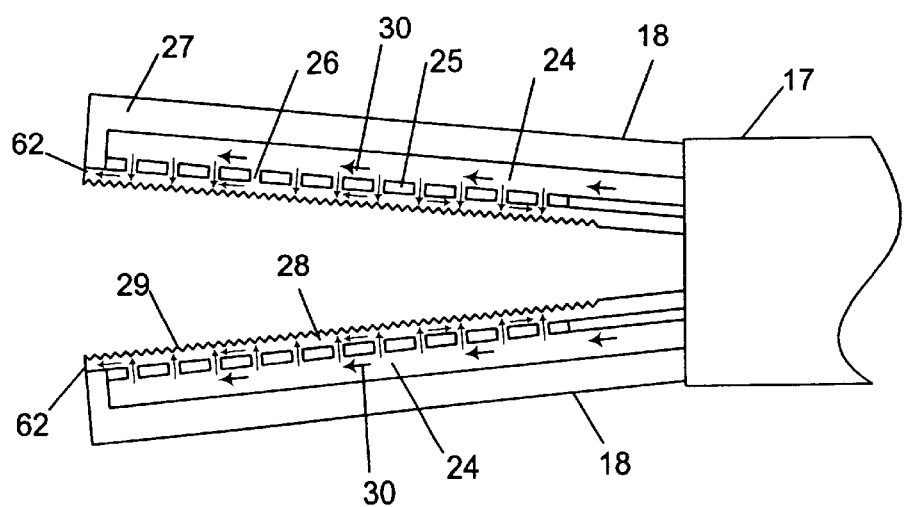
FIG. 8 is a schematic close-up section side view of the tip of the device shown in FIG. 7.

FIG. 8 shows a schematic close-up section view of the two jaws 18 at the distal tip of the shaft 17. In a preferred embodiment, each jaw 18 includes an electrode 25, a manifold 24, and a plurality of holes 26 in the electrode. Each jaw 18 further includes a jaw surface 29 that contacts the tissue to be treated. In the embodiment illustrated in FIG. 8, the jaw surface 29 is textured, so that it is capable of grasping the tissue to be treated. However, the jaw surface 29 need not be textured, and can include any type of desired surface configuration, such as serrations and the like, or can be provided with a smooth surface. In use, saline flows in a manifold 24 in the direction of arrows 30, wherein the manifold 24 distributes saline flow evenly to a plurality of holes 26 that are made in the jaw 18. Preferably, most of the structural material of each jaw 18 is fabricated from a material that is non-conductive electrically, such as nylon or other polymer such as liquid crystal polymer. This non-conductive material is shown in the figure as reference number 27. Further, in some embodiments, the jaw surface 29 can be fabricated from a nonconductive material. In a preferred embodiment, each jaw 18 further includes a groove 28 that is recessed from the jaw surface 29. In this embodiment, after the saline flows through the holes 26, it flows in the groove 28. When tissue is grasped between the jaws, saline can flow in the groove 28 between the electrode and the tissue, and exit through exit grooves 62 that are open to the outside at the proximal end of the jaws 18.

Figure 9:
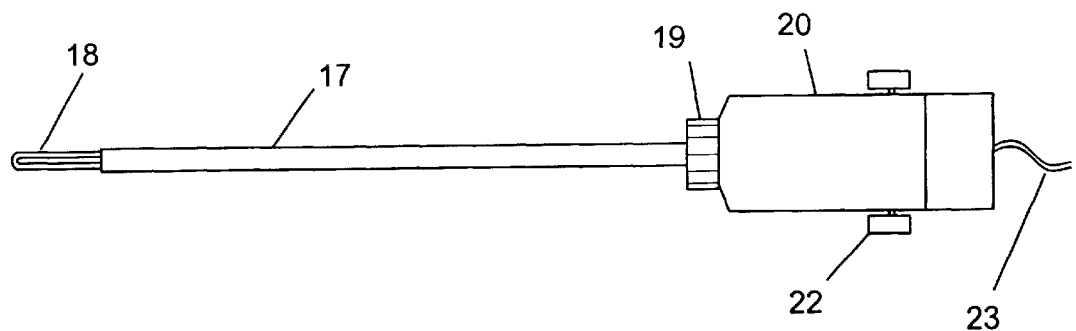
FIG. 9 is a schematic top view of the bipolar electrosurgical device shown in FIG. 7.
Figure 10:
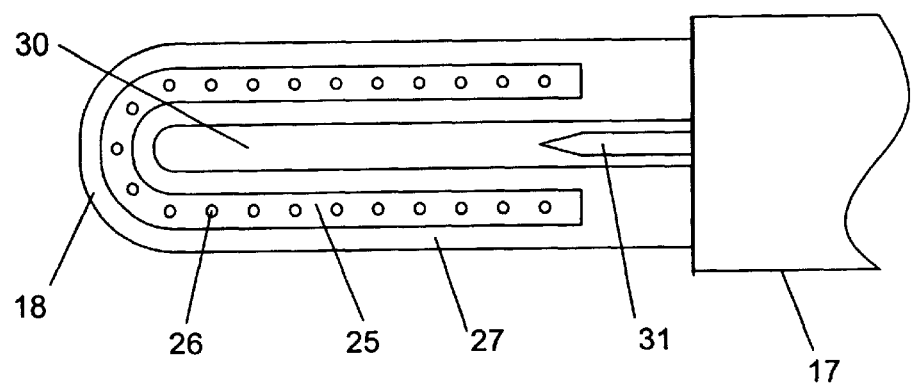
FIG. 10 is a schematic close-up section top view of the tip of the device shown in FIG. 9.

FIG. 9 shows an overall schematic top view of the electrosurgical device shown in FIGS. 7 and 8. As shown in FIG. 9, the jaws 18 can be provided in a loop configuration. FIG. 10 shows a close-up section of one of the loop jaws 18. In this embodiment, the jaws 18 are provided in a loop configuration to create a space 30 that allows a cutting mechanism 31 to move proximally and distally within the space 30. One of skill in the art would comprehend that the electrode configuration shown in FIG. 9 is simply an exemplary configuration, and the electrode need not be formed of two loops. For example, the electrosurgical device need not include a cutting mechanism, and the electrodes in these embodiments would not be required to include a space or recess for passage of the cutting mechanism. The invention contemplates any suitable electrode configuration used to treat tissue with RF energy and conductive fluid.

Figure 11:
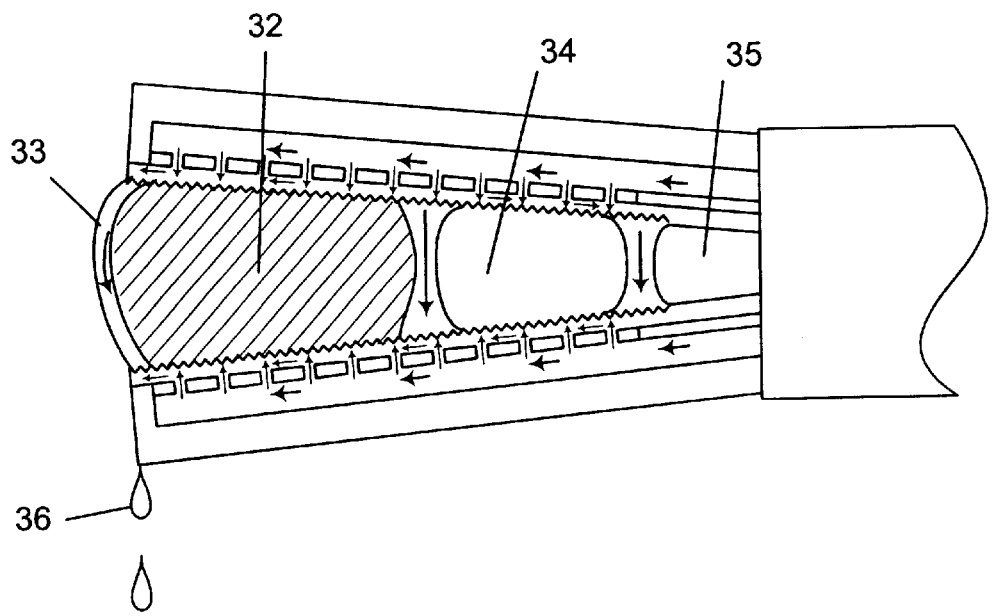
FIG. 11 is a schematic close-up section side view of the electrodes of the device shown in FIG. 9 showing saline shunting without boiling of the saline.

If the saline that flows from one electrode to the other is not boiling in any significant manner, a large fraction of the RF energy can be diverted away from target tissue. This "stealing" of RF energy tends to dramatically slow down the process of coagulating tissue and producing the desired hemostasis or aerostasis of the tissue. This situation is illustrated in FIG. 11. In this embodiment, tissue 32 grasped between the jaws 18 does not fill the jaws. Areas 34 and 35 show areas of air between the jaws 18. Saline liquid flows from the top electrode jaw to the lower electrode jaw in several locations: at area 33, located at the distal end of the jaws 18, at locations between tissue 32 and area 34, and between areas 34 and 35. These locations of saline flow between areas 34 and 35 represent the closest gap between jaws (area 35) and flow of saline along the tissue boundary 32, which are the most likely areas for saline flow between the jaws 18. Since most of the saline is not boiled, excess saline 36 drips off the lower jaw.

Figure 11A:
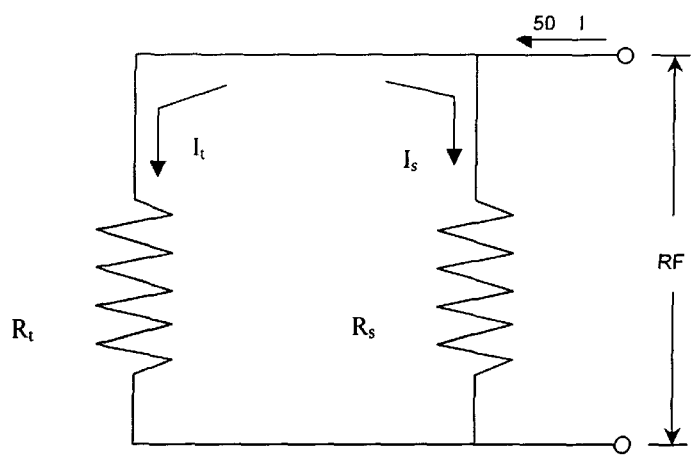
FIG. 11a is a diagram that describes the equivalent electrical circuit for tissue in parallel with a single saline shunt.

The saline shunting scenario can also be explained by using an electrical circuit as shown in FIG. 11a. Electrically, the tissue and the saline fluid shunt can be modeled as resistors in parallel. Using Ohm's Law one can calculate the percentage of total RF power that is dissipated in the saline shunt as:

$$\% \text{ RF Power} = \frac{100}{[1 + R_s/R_t]}$$

Figure 11B:
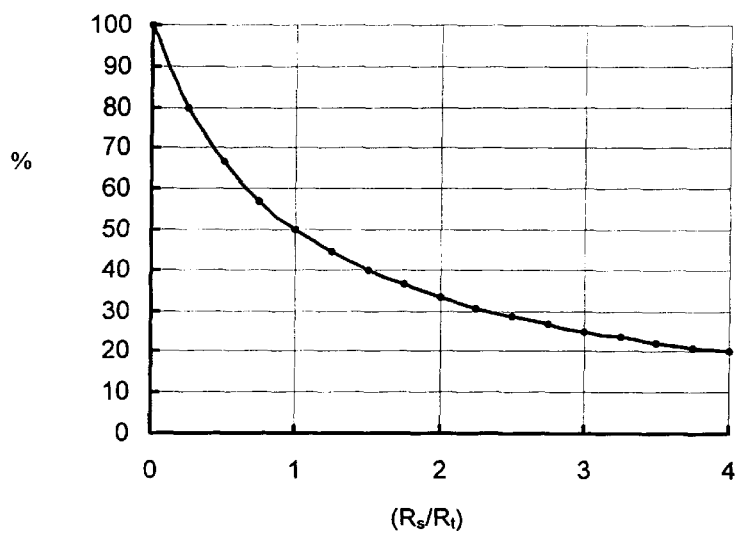
FIG. 11b is a graph that describes the relationship of ratio of saline to tissue resistance ($R_s/R_t$) and percent power shunted into saline.

In the embodiment illustrated in FIG. 11a, the total current (I) 50 from source 54 is split between two resistors, tissue electrical resistance ($R_t$), and saline shunt electrical resistance ($R_s$). This relationship is shown in the schematic graph of FIG. 11b, which shows the relationship of the ratio of saline to tissue resistance ($R_s/R_t$) to percent of power shunted into saline. As shown in the figure, when the resistance of the saline is equal to the tissue ($R_s/R_t=1$), half the power is shunted into the saline. For example, when the resistance of the saline is four times that of the tissue, then only 20% of the power is shunted into the saline.

Figure 12:
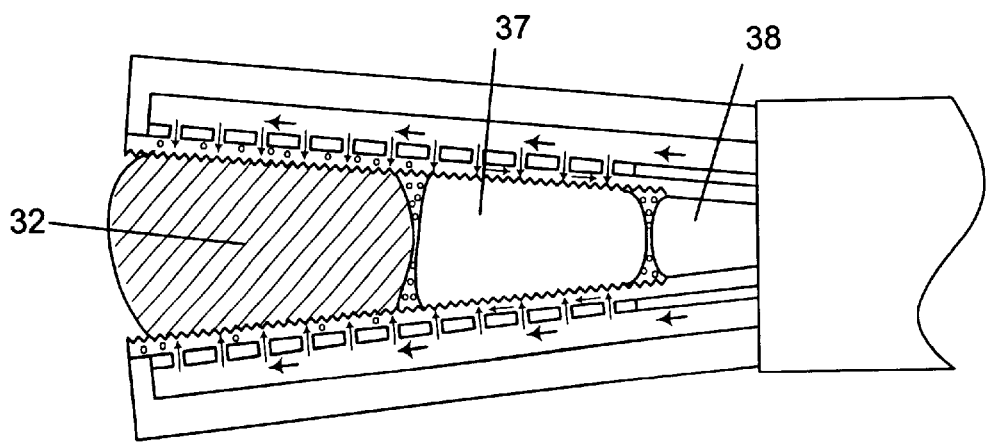
FIG. 12 is a schematic close-up side section view of the electrodes of the device shown in FIG. 9 showing a large percentage of the saline boiling at the tissue treatment site.

One benefit of the flow rate control strategy described herein, where a high % boiling is maintained, is that the flow of saline from one electrode to the other is either eliminated altogether because all the flow boils off at the electrode/tissue interface, or a large fraction of the flow boils as it flows toward the other electrode. This second case is illustrated in FIG. 12, that is, where a large fraction of the saline flow boils as it flows toward the other electrode. Note that in comparison to FIG. 11, there is less saline flowing from the top jaw to the lower jaw, and where there is flow it is actively boiling, as indicated by the vapor bubbles shown in several locations 37 and 38. According to the invention, boiling of a large fraction of the saline assures that most of the RF power will be directed into the tissue to achieve coagulation in the fastest time.

One aspect of the control strategy of the invention is that the flow of saline is preferably primarily directed spatially against or very near the target tissue that is to receive the RF power. If the flow rate is not near where the RF power is turned into heat, the saline is not capable of protecting the tissue from desiccation by dissipating excess heat in the boiling process. Therefore, in a preferred embodiment, the flow of conductive fluid is directly primarily at the tissue treatment site.

Use

Figure 13:
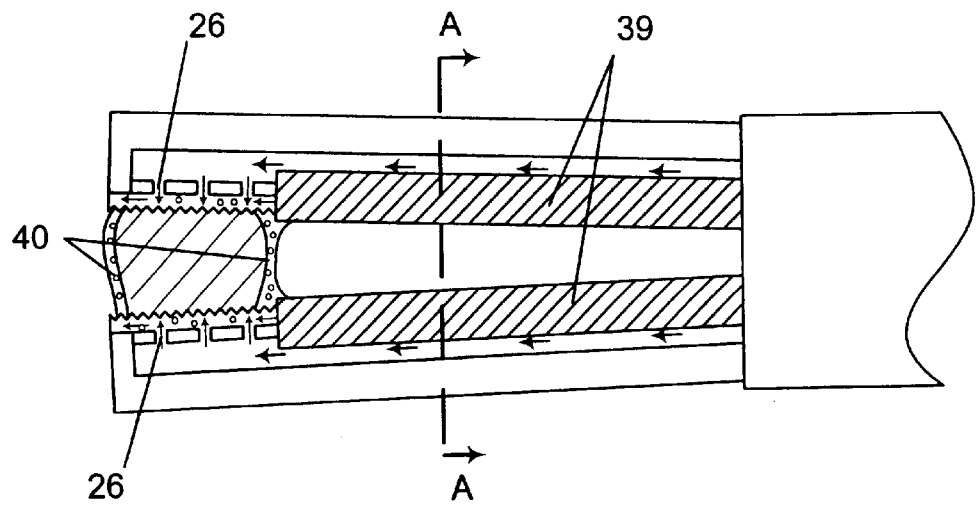
FIG. 13 is a schematic close-up side section view of electrodes of the device shown in FIG. 9 showing two gutters slid out to direct saline flow distally toward tissue.

Typically a surgeon will grasp a small amount of tissue with the very tip of the device as shown in FIG. 13. If the electrode jaws are long relative to the length of the tissue segment being grasped, then saline exiting of holes 26 in the proximal part of the jaws may not be able to flow to the tip, but may leak out along the upper jaw. Though surface tension will act to keep saline flow in the groove 28, gravity can tend to cause the saline collect and flow down directly to the opposing jaw. This would result in the undesirable effects mentioned above. By providing two slidable gutters 39, the flow of saline can be collected and directed distally toward the tissue. In this embodiment, the saline can flow from one jaw to the other in areas 40, located on each side of the tissue being grasped, but with a large percentage boiling before reaching the other jaw. According to this embodiment, the gutters 39 can be fabricated from any material that is non-conducting, for example, plastic. The gutters can slide toward the distal end of the device as part of the activation of lever 21 shown in FIG. 7, to be stopped automatically by the presence of tissue. Alternatively the gutters 39 can be slid forward as part of a separate mechanism action. The gutters 39 can be fabricated from any suitable material that is non-conducting, for example, plastic.

Figure 14:
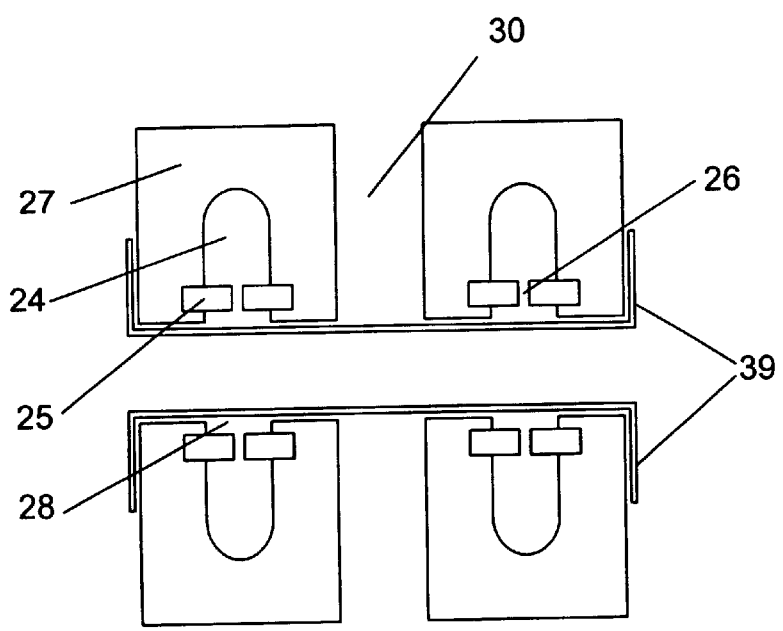
FIG. 14 is a schematic close-up cross-section view along line A—A of FIG. 9, showing the two gutters positioned to collect and direct saline flow distally.

FIG. 14 shows a schematic cross-sectional view of the gutters shown in FIG. 13. The cross-section in FIG. 14 illustrates the nonconducting portion 27 of the jaw 18, the saline manifold 24, the electrodes 25, holes 26, groove 28, space 30 for the cutting mechanism, and gutters 39. Near the distal end of the gutters, exit grooves 62 in the gutter can allow saline to flow through and onto the edge of the tissue even if the gutter is pressed snuggly against the tissue (shown in FIG. 8).

Figure 15:
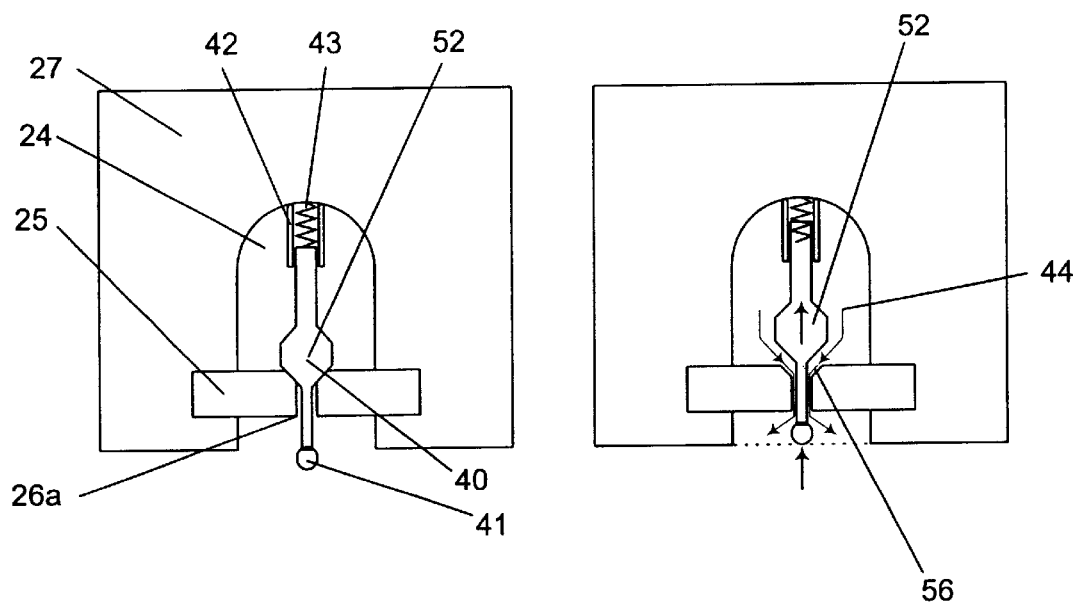
FIG. 15 is a schematic close-up cross-section view of one embodiment of the jaws of the device shown in FIG. 9, wherein the jaws include a tissue-activated valve.
Figure 16:
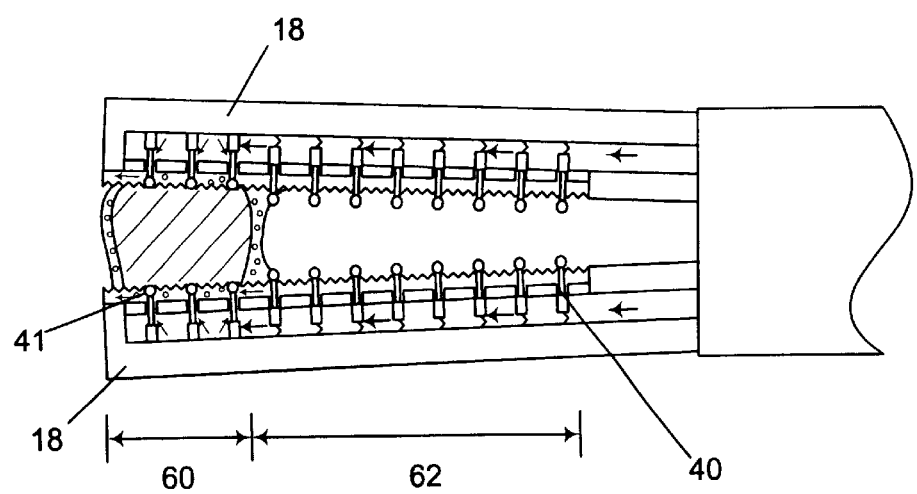
FIG. 16 is a schematic close-up side section view of one embodiment of the jaws of the device shown in FIG. 9, wherein the jaws include tissue-activated valves to direct flow distally.

FIG. 15 and FIG. 16 illustrate an alternative embodiment of the electrosurgical device of the invention. In this embodiment, the electrosurgical device includes a mechanism for directing saline flow to where tissue is being heated using RF energy. Preferably, the mechanism for directing saline flow comprises one or more tissue activated valves. In FIG. 15, the jaw 18 of the device includes a pin 40 that is configured with a bulged portion 52 in the middle section of the plunger pin 40, so that the pin 40 can seat into a counter-sunk hole 26a in the electrode 25. Pin 40 preferably further includes a pin tip 41 that contacts tissue. Preferably, the pin tip 41 is rounded or atraumatic to reduce tissue trauma. As illustrated in the figure, counter-sunk hole 26a includes a recessed portion 56 that is configured to receive the bulged portion 52, such that when seated within the recessed portion 56, the pin 40 prevents conductive fluid flow from the manifold 24 to the tissue being treated. Preferably, a guide tube 42 holds the pin 40 in position, and spring 43 provides force to push the bulged portion 52 of pin 40 into the recessed portion 56 and seal off the flow of saline from the manifold region 24. In use, the pin tip 41 contacts tissue when the jaws 18 compress tissue. When tissue is compressed, the tissue contacts the tip 41 and pushes the pin 40 upwards, unseating the bulged portion 52 of the pin 40 from the recessed portion 56, and allowing saline to flow in direction of arrows 44 through the annular space between the pin 40 and the counter-sunk hole 26a.

FIG. 16 shows a schematic view of one embodiment wherein a series of such tissue-activated valves functions to deliver saline flow only to areas of the jaws where tissue is compressed and to be RF-heated. Referring to FIGS. 15 and 16, tissue is compressed in the area labeled 60, and the holes 26a are open to allow saline flow to the tissue treatment site. As described above, tissue contacts tip 41, thereby pushing pin 40 upwards, unseating the bulged portion 52 of the pin 40 from the recessed portion 56 (shown in FIG. 15). This interaction allows saline to flow from the device 5a to the tissue being treated. In the area labeled 62 in the figure, tissue is not compressed between jaws 18 of the device 5a, and therefore the holes 26a are closed to the flow of saline from the device 5a. Because the tips 41 of pins 40 do not contact tissue, the pin 40 is not forced from its seated position within recessed portion 56 of the hole 26a (shown in FIG. 15).

Generally, the holes 26 or 26a of the electrode 25 supply conductive fluid to the treatment site. In an alternative embodiment, these holes are provided in the form of porous material such as metal. In this embodiment, the electrodes do not include discrete holes; rather, the electrode surface itself is porous to allow infusion of the conductive solution to the treatment site. Porous sintered metal is available in many materials (such as, for example, 316L stainless steel, titanium, Ni-Chrome, and the like) and shapes (such as cylinders, discs, plugs, and the like) from companies such as Porvair, located in Henderson, N.C.

Porous metal components can be formed by a sintered metal powder process or by injection molding a two-part combination of metal and a material that can be burned off to form pores that connect (open cell) to each other. Such methods are known in the art. In this embodiment, conductive fluid will flow out of the electrode everywhere the pores are open. Preferably, the exterior (that is, the portions of the components that do not comprise the portion of the device involved in tissue treatment) of such porous metal electrode components can be covered with a material that fills the pores and prevents both the flow of saline and the passing of electrical energy. Alternatively, the device can include gutters to prevent the flow of saline in areas where it is desired to prevent saline flow.

In yet another embodiment, a porous polymer is used in place of the porous metal. Although the polymer is non-conductive, the conductive solution provided will conduct the RF energy across the porous polymer wall and to the tissue to be treated. Suitable materials include high temperature open cell silicone foam and porous polycarbonates, among others. Porous ceramics also fall into this category, since they could distribute conductive fluid flow, withstand high temperatures and be machinable or moldable for manufacturing purposes. Preferably, the material used transmits both fluid flow and electrical energy; thus, materials with properties between high-electrical conductivity metals and low electrical conductivity polymers are also contemplated, such as porous carbon-filled polymers. In these embodiments, conductive fluid flow is distributed along the length of the electrodes, where porous material is used to fabricate the electrodes. All or a portion of the electrodes can be porous according to the invention.

While the invention has been described in relation to a bipolar electrosurgical device, it will be readily apparent that other electrosurgical devices can be easily adapted to be used in connection with the invention. For example, the electrosurgical device 5 in FIG. 1 can, in another embodiment, be provided as a monopolar device. In this embodiment, one of the wires going to the bipolar device would instead go to a ground pad dispersive electrode located on the patient's back or other suitable anatomical location. Minimally, the electrosurgical device will be capable of delivering RF power and conductive solution to tissue. For example, the device can comprise a straight needle having an interior lumen for transmitting conductive solution to the tissue. Alternatively, the electrosurgical device can comprise other configurations such as loops, forceps, blades, and the like.

Other suitable electrosurgical devices that can be used in connection with the invention described herein include, but are not limited to, devices described in U.S. patent application Ser. No. 09/668,403 (filed Sep. 22, 2000), U.S. Pat. No. 5,897,553 (issued Apr. 27, 1999), U.S. Pat. No. 6,063,081 (issued May 16, 2000), and U.S. Pat. No. 6,096,037 (issued Aug. 1, 2000).

Moreover, it will be readily apparent that other means can be used to provide heat to the tissue, in addition to the radio frequency power described herein.

One or more of the features of the previously described system can be built into a custom RF generator. This embodiment can provide one or more advantages. For example, this type of system can save space and reduce overall complexity for the user. This system can also enable the manufacturer to increase the power delivered into low impedance loads, thereby further reducing the time to achieve the desired tissue effects. This changes the curve of FIG. 5, by eliminating or reducing the slope of the low impedance ramp of power versus impedance.

To effectively treat thick tissues, it can be advantageous to have the ability to pulse the RF power on and off. Under some circumstances, the temperature deep in tissue can rise quickly past the 100° C. desiccation point even though the electrode/tissue interface is boiling at 100° C. This manifests itself as "popping," as steam generated deep in the tissue boils too fast and erupts toward the surface. In one embodiment of the invention, a switch is provided on the control device or custom generator to allow the user to select a "pulse" mode of the RF power. Preferably, the RF power system in this embodiment is further controlled by software.

In some embodiments, it can be desirable to control the temperature of the conductive fluid before it is released from the electrosurgical device. In one embodiment, a heat exchanger is provided for the outgoing saline flow to either heat or chill the saline. Pre-heating the saline to a predetermined level below boiling reduces the transient warm-up time of the device as RF is initially turned on, thereby reducing the time to cause coagulation of tissue. Alternatively, pre-chilling the saline is useful when the surgeon desires to protect certain tissues at the electrode/tissue interface and treat only deeper tissue. One exemplary application of this embodiment is the treatment of varicose veins, where it is desirable to avoid thermal damage to the surface of the skin. At the same time, treatment is provided to shrink underlying blood vessels using thermal coagulation. The temperature of the conductive fluid prior to release from the surgical device can therefore be controlled, to provide the desired treatment effect.

In another embodiment, the flow rate controller is modified to provide for a saline flow rate that results in greater than 100% boiling at the tissue treatment site. For example, the selection switch 12 of the flow rate controller 11 (shown in FIG. 1) can include settings that correspond to 110%, 120% and greater percentages of boiling. These higher settings can be of value to a surgeon in such situations as when encountering thick tissue, wherein the thickness of the tissue can increase conduction away from the electrode jaws. Since the basic control strategy neglects heat conduction, setting for 100% boiling can result in 80% of 90% boiling, depending upon the amount of conduction. Given the teachings herein, the switch of the flow rate controller can accommodate any desirable flow rate settings, to achieve the desired saline boiling at the tissue treatment site.

Some embodiments of the invention can provide one or more advantages over current electrosurgical techniques and devices. For example, the invention preferably achieves the desired tissue effect (for example, coagulation, cutting, and the like) in a fast manner. In a preferred embodiment, by actively controlling the flow rate of saline, both in quantity (Q vs. P) and location (for example, using gutters to direct fluid distally to tissue, using holes to direct flow of fluid, or other similar methods) the electrosurgical device can create a hot non-desiccating electrode/tissue interface and thus a fast thermally induced tissue coagulation effect.

The invention can, in some embodiments, deliver fast treatment of tissue without using a temperature sensor built into the device or a custom special-purpose generator. In a preferred embodiment, there is no built-in temperature sensor or other type of tissue sensor, nor is there any custom generator. Preferably, the invention provides a means for controlling the flow rate to the device such that the device and flow rate controller can be used with a wide variety of general-purpose generators. Any general-purpose generator is useable in connection with the fluid delivery system and flow rate controller to provide the desired power; the flow rate controller will accept the power and constantly adjust the saline flow rate according to the control strategy. Preferably, the generator is not actively controlled by the invention, so that standard generators are useable according to the invention. Preferably, there is no active feedback from the device and the control of the saline flow rate is "open loop." Thus, in this embodiment, the control of saline flow rate is not dependent on feedback, but rather the measurement of the RF power going out to the device.

In another aspect, the invention preferably provides an electrosurgical device design that is capable of quickly and effectively sealing a wide variety of tissue segment sizes. The electrosurgical device provides a number of characteristics that improve the ability to treat a wide variety of tissue size and thickness. For example, a preferred embodiment provides the ability to control the saline flow towards a high percentage boiling, for example, 80–100%. This reduces shunting of the RF by boiling off saline before it could flow to the other electrode, or by boiling the saline as it is in the process of flowing to the other electrode. In another aspect, one preferred embodiment includes gutters in connection with the electrodes. In this embodiment, saline flow is directed toward the tissue treatment site, thereby providing all or substantially all of the conductive fluid to the treatment site. Thus, the tissue being treated is sufficiently "protected" from desiccation by utilizing the controlled conductive fluid boiling described herein. Preferably, the tissue-activated jaws offer another way to provide the conductive fluid in proximity to where the RF power is turned into heat.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents.

All publications and patent documents cited in this application are incorporated by reference in their entirety for all purposes to the extent they are not inconsistent with the teachings herein.

We claim:

1. A system for treating tissue comprising:
   a) a power measurement device;
   b) a flow rate controller coupled to the power measurement device; and
   c) an electrosurgical device configured and arranged to provide radio frequency power and conductive fluid to the tissue,
   wherein the flow rate controller is configured and arranged to modify a flow rate of the conductive fluid to the tissue, based on signals from the power measurement device and heat used to warm the conductive fluid and heat used to convert the conductive fluid vapor.

2. The system according to claim 1 wherein the flow rate controller modifies the flow rare of the conductive fluid to the tissue based on heat used to warm the conductive fluid and heat used to convert the conductive fluid to vapor using the relationship:

$$K = \frac{1}{\{\rho c_p \Delta T + \rho h_v Q_b / Q_l\}}$$

where $\rho$ is density of the conductive fluid that is heated, $C_p$ is the specific heat of the conductive fluid, $Q_1$ is the flow rate of the conductive fluid that is heated, $\Delta T$ is temperature rise of the conductive fluid, $h_v$ is heat of vaporization of the conductive fluid, and $Q_b$ is the flow rate of conductive fluid that boils.

3. The system according to claim 1 wherein the conductive fluid comprises saline and the flow rate controller is configured and arranged to modify the flow rate of saline.

4. The system according to claim 1 wherein the electrosurgical device comprises a bipolar electrosurgical device.

5. The system according to claim 1 further comprising a generator that provides radio frequency power to the electrosurgical device through the power measurement device.

6. A device for modifying flow rare of conductive fluid to tissue based on measurement of radio frequency power delivered to the tissue, the device comprising:
   a flow rate controller configured and arranged to modify flow rate of the conductive fluid to the tissue, based on heat used to warm the conductive fluid and heat used to convert the conductive fluid to vapor.

7. The device according to claim 6 wherein the flow rate controller modifies the flow rate of the conductive fluid to the tissue based on heat used to warm the conductive fluid and heat used to convert the conductive fluid to vapor using the relationship:

$$K = \frac{1}{\{\rho c_p \Delta T + \rho h_v Q_b / Q_l\}}$$

where $\rho$ is density of the conductive fluid that is heated, $C_p$ is the specific heat of the conductive fluid, $Q_1$ is the flow rate of the conductive fluid that is heated, $\Delta T$ is temperature rise of the conductive fluid, $h_v$ is heat of vaporization of the conductive fluid, and $Q_b$ is the flow rate of conductive fluid that boils.

8. The device according to claim 6 wherein the conductive fluid comprises saline and the flow rate controller is configured and arranged to modify the flow rate of saline to the tissue.

9. A device for treating tissue using radio frequency power and conductive fluid, the device comprising:
   a) a sensing device, and
   b) a processor coupled to the sensing device, wherein the processor is configured and arranged to adjust flow rate of the conductive fluid to the tissue, by determining a level of radio frequency power applied to the tissue using the sensing device, and adjusting the flow rate of the conductive fluid to the tissue based on heat used to warm the conductive fluid and heat used to convert the conductive fluid to vapor.

10. The device according to claim 9 wherein the processor of the device is configured and arranged to adjust the flow rate of the conductive fluid to the tissue based on heat used to warm the conductive fluid and heat used to convert the conductive fluid to vapor using the relationship:

$$K = \frac{1}{\{\rho c_p \Delta T + \rho h_v Q_b / Q_l\}}$$

where $\rho$ is density of the conductive fluid that is heated, $C_p$ is the specific heat of the conductive fluid, $Q_1$ is the flow raze of the conductive fluid that is heated, $\Delta T$ is temperature rise of the conductive fluid, $h_v$ is heat of vaporization of the conductive fluid, and $Q_b$ is the flow rate of conductive fluid that boils.

11. The device according to claim 9 wherein the conductive fluid comprises saline and the device uses radio frequency power and saline to treat the tissue.

12. A system for treating tissue comprising:
    a) a power measurement device;
    b) a flow rate controller coupled to the power measurement device;
    c) a flow control device coupled to the flow rate controller; and
    d) an electrosurgical device coupled to the flow control device and the power measurement device, wherein the electrosurgical device is configured and arranged to provide radio frequency power and conductive fluid to the tissue,
    wherein the flow rate controller is configured and arranged to modify a flow rate of the conductive fluid to the electrosurgical device, based on signals from the power measurement device and heat used to warm the conductive fluid and heat used to convert the conductive fluid to vapor.

13. The system according to claim 12 wherein the flow control device comprises a pump.

14. The system according to claim 13 wherein the pump comprises a peristaltic pump.

15. The system according to claim 13 wherein the pump comprises a syringe pump.

16. A system according to claim 12 wherein the flow rate controller is configured and arranged to modify the flow rate of the conductive fluid to the electrosurgical device based on heat used to warm the conductive fluid and heat used to convert the conductive fluid to vapor using the relationship:

$$K = \frac{1}{\{\rho c_p \Delta T + \rho h_v Q_b / Q_l\}}$$

where $\rho$ is density of the conductive fluid that is heated, $C_p$ is the specific heat of the conductive fluid, $Q_1$ is the flow rate of the conductive fluid that is heated, $\Delta T$ is temperature rise of the conductive fluid, $h_v$ is heat of vaporization of the conductive fluid, and $Q_b$ is the flow rate of conductive fluid that boils.

17. The system according to claim 12 wherein the conductive fluid comprises saline and the electrosurgical device is configured and arranged to provide radio frequency power and saline to the tissue.

18. The system according to claim 12 wherein the electrosurgical device comprises a bipolar electrosurgical device.

19. The system according to claim 18 wherein the bipolar electrosurgical device comprises opposing jaws and slidable gutters disposed on the opposing jaws.

20. The system according to claim 18 wherein the bipolar electrosurgical device comprises a cutting mechanism.

21. The system according to claim 18 wherein the bipolar electrosurgical device comprises tissue activated valves.

22. A system for treating tissue comprising:
radio frequency power provided from a power source at a power level;
an electrically conductive fluid provided from a fluid source at a fluid flow rate;
an electrosurgical device configured to provide the radio frequency power with the electrically conductive fluid to the tissue; and
a flow rate controller configured to modify the fluid flow rate of the electrically conductive fluid based on boiling of the conductive fluid.

23. The system for treating tissue according to claim 22 wherein the fluid flow raze is modified based on one of initiating, increasing, decreasing and eliminating boiling of the conductive fluid.

24. The system for treating tissue according to claim 22 wherein the fluid flow rate is modified based on an amount of boiling of the conductive fluid.

25. The system for treating tissue according to claim 22 wherein the fluid flow rate is modified based on an onset of boiling of the conductive fluid.

26. A system for treating tissue comprising:
radio frequency power provided from a power source at a power level;
an electrically conductive fluid provided from a fluid source at a fluid flow rate;
an electrosurgical configured to provide the radio frequency power with the electrically conductive fluid to the tissue; and
a flow rate controller configured to modify the fluid flow rate of the electrically conductive fluid based on heat used to warm the conductive fluid to an onset of boiling and heat used to convert at least a portion of the conductive fluid to vapor.

27. A system for treating tissue comprising:
radio frequency power provided from a power source at a power level;
an electrically conductive fluid provided from a fluid source at a fluid flow rate;
an electrosurgical device configured to provide the radio frequency power with the electrically conductive fluid to the tissue; and
a flow rate controller configured to modify the fluid flow rate of the electrically conductive fluid based on one of initiating, increasing, decreasing and eliminating a boiling of the fluid.

28. A system for treating tissue comprising:
radio frequency power provided from a power source at a power level;
an electrically conductive fluid provided from a fluid source at a fluid flow rate;
an electrosurgical device configured to provide the radio frequency power with the electrically conductive fluid to the tissue; and
a flow rate controller configured to modify the fluid flow rate of the electrically conductive fluid based on an amount of boiling of the conductive fluid.

29. The system for treating tissue according to claim 22 wherein the fluid flow rate is modified in an open feedback loop.

30. The system for treating tissue according to claim 22 wherein the fluid flow rate from the flow rate controller is manually adjustable to modify the fluid flow rate.

* * * * *

UNITED STATES PATENT AND TRADEMARK OFFICE
CERTIFICATE OF CORRECTION

PATENT NO. : 6,702,810 B2
DATED : March 9, 2004
INVENTOR(S) : McClurken et al.

It is certified that error appears in the above-identified patent and that said Letters Patent is hereby corrected as shown below:

Column 17,
Lines 17-18, "the conductive fluid vapor," should read -- the conductive fluid to vapor. --

Column 20,
Line 1, "an electrosurgical configured" should read -- an electrosurgical device configured --

Signed and Sealed this

Sixth Day of July, 2004

JON W. DUDAS
*Acting Director of the United States Patent and Trademark Office*